United States Patent [19]
Thomson et al.

[11] Patent Number: 5,821,017
[45] Date of Patent: Oct. 13, 1998

[54] METHOD OF DEPOSITION

[75] Inventors: James Thomson; James Cairns, both of Dundee, Scotland

[73] Assignee: The University Court of the University of Dundee, Dundee, United Kingdom

[21] Appl. No.: 436,394

[22] PCT Filed: Nov. 19, 1993

[86] PCT No.: PCT/GB93/02391

§ 371 Date: Aug. 18, 1995

§ 102(e) Date: Aug. 18, 1995

[87] PCT Pub. No.: WO94/11787

PCT Pub. Date: May 26, 1994

[30] Foreign Application Priority Data

Nov. 19, 1992 [GB] United Kingdom .................. 9224233
Mar. 27, 1993 [GB] United Kingdom .................. 9306446
Aug. 26, 1993 [GB] United Kingdom .................. 9317750

[51] Int. Cl.⁶ ........................................... G03C 3/00
[52] U.S. Cl. ................................ 430/9; 427/555; 427/584
[58] Field of Search .................................... 427/584, 585, 427/226, 229, 252, 555, 490; 156/643; 430/9

[56] References Cited

U.S. PATENT DOCUMENTS

| | | | |
|---|---|---|---|
| 4,444,801 | 4/1984 | Hongo et al. | 427/10 |
| 4,714,627 | 12/1987 | Puddephatt et al. | 427/53.1 |
| 4,869,930 | 9/1989 | Clarke et al. | 427/252 |
| 5,104,481 | 4/1992 | Dooley et al. | 156/643 |
| 5,104,684 | 4/1992 | Tao et al. | 427/38 |
| 5,169,579 | 12/1992 | Marcus et al. | 156/272.8 |
| 5,230,970 | 7/1993 | Atwood et al. | 430/5 |
| 5,407,710 | 4/1995 | Baum et al. | 427/555 |

FOREIGN PATENT DOCUMENTS

| | | |
|---|---|---|
| 90/02827 | 3/1990 | WIPO . |
| 90/06315 | 6/1990 | WIPO . |

OTHER PUBLICATIONS

Research Disclosure, Mar. 1992, Havant, UK, pp. 211 XP000301117, Anonymous, "Pin Repair of MLC Substrate I/O Pads by Focused Ion Beam Techniques".

T. Mole, E.A. Jeffery, "Organoaluminium Compounds", Mar. 1972, Elsevier Publishing Company, Amsterdam, The Netherlands.

*Primary Examiner*—S. Rosasco
*Attorney, Agent, or Firm*—Ratner & Prestia

[57] ABSTRACT

There is described a method of chemically depositing a substance. The method is of utility in the direct manufacture of integrated circuits and in the manufacture of a photomask for use in production of integrated circuits. The method involves the use of a compound which degrades into a deposit and a residue when a radiant beam (e.g., a laser beam) or a particle beam (e.g., an electron beam) is applied. The residue and any unreacted compound may be washed off the substrate to which it has been applied. Nanoscale dimensions of the deposit can be achieved. A particularly suitable organometallic compound is tetra-sec butyl diaurum difluoride.

9 Claims, 28 Drawing Sheets

METHOD OF DEPOSITION

This invention relates to a method of depositing substances, for example metals. The method may be used in the manufacture of integrated circuits and photomasks.

Modern technological demands in integrated circuitry, for example opto-electronics and electronic surgical implants, now require methods by which ultra fine metal lines of submicron dimensions can be deposited onto inert substrate materials. There is a considerable demand for submicron technology in a wide variety of disciplines, but there are many difficulties in developing nanoscale metal deposition processes by conventional lithographic methods. Lithography is the process by which a pattern is transferred to the surface of a substrate material. Before this process can occur a photomask has to be prepared which defines the pattern ultimately. to be achieved on the substrate layer.

Conventionally the photomasks required in the manufacture of integrated circuits are made by applying a film layer of metal, usually chromium since this resists scratching or etching and has good adhesion properties, by metal vapour deposition to a highly pure quartz substrate which has been polished to give an extremely flat surface. The exposed metal is then covered with electron beam resist (which is a material that is sensitive to a beam of electrons and is disrupted on exposure thereto) by placing a drop of resist in the middle of a spinning disk of mask material. The resist is then baked and dried in an oven. The usual electron beam resist is polybutylsulphone (PBS).

An electron beam is directed at the resist face of the resist/metal/substrate composite to degrade portions of the resist, leaving unaffected a pattern required for the integrated circuit. The degraded resist is then dissolved away using a proprietary etchant to expose the layer of metal in the areas where the resist has been degraded, and this is subjected to wet etching by ceric ammonium nitrate to remove the metal and expose the quartz substrate. The remaining resist is then burnt off from the residual metal, resulting in a product through which light can pass apart from the areas masked by metal.

The photomask thus produced is used to define a pattern on a silicon chip coated with photoresist, by passing ultraviolet light through the photomask to degrade the photoresist in the defined areas.

This method of manufacturing photomasks has a number of disadvantages. For example, the dissolution of the degraded photoresist may not be entirely uniform, and while the result is adequate for many products current computer technology demands increasingly dense patterns on integrated circuits and therefore higher-definition photomasks, down to the nanoscale level.

A further area of loss of definition is the wet etch process for removing the unwanted chromium. The etch material attacks the upper, exposed face of the chromium but as it penetrates into the chromium layer its effect is not unidirectional, so instead of producing vertical walls for the residual chromium it erodes and undercuts these walls. This can produce a scattering effect on the ultraviolet light during manufacture of the integrated circuits, reducing definition of the applied pattern. This is one of the principal problems in mask-making.

Where several photomasks are used successively in the manufacture of a chip, accurate registration of each mask is absolutely essential so that each feature appears in the correct place on the finished chip. Problems in epitaxy can cause pattern shift and thus registration. Usually registration is accurate to +/− 0.2 $\mu$m. Registration problems, epitaxy growth problems, undercutting, constructive and destructive interference during lithographic process at micron and submicron dimensions, all contrive to indicate that maskmaking at nanometer dimensions may require an entirely new manufacturing process.

For nanoscale circuits, conventional methods using metallic inks do not as yet possess the specifications which can ensure the deposition of accurate straight lines of high specification, and the formation of perfect right angles rather than arcs during integrated circuit manufacture. The low specification of the conventional process of metallisation can result in circuit overlap and circuit breakage which cannot be tolerated when scribing nanoscale circuits. Further, when ultra fine lines are required to carry current it is a fundamental requirement that the circuit integrity remains intact, and hence conductive materials which are oxidized are not ideally suited to operate at such dimensions.

According to the present invention there is provided a method of chemical deposition comprising depositing on a substrate an organometallic fluoride compound which degrades under the effect of a radiant or particle beam to produce a deposit, applying to selected surface areas of said compound such a radiant or particle beam and removing the degraded compound and the unaffected compound from the substrate. The deposit is left upon the substrate.

The process of the present invention causes degradation of the compound only where contacted by the radiant or particle beam. In other words, the dimensions of the deposit caused by degradation of the compound is proportional to the focal width of the irradiating beam. Nanoscale dimensions may be achieved by the process of the present invention.

Where the compound degrades to form a deposit of a metallic or other conductive substance, then the method may be used to manufacture integrated circuits directly on the substrate. The deposit is preferably a metal or metal alloy, and mention may be made of metals such as gold, tin and chromium, or the deposit may be a conductive non-metal or semi-metal, such as germanium.

In a further aspect there is provided a method of manufacture of an integrated circuit, said method comprising applying to a substrate a compound which degrades under the effect of a radiant or particle beam to produce a conductive, preferably metallic deposit, applying to selected surface areas of said compound such a radiant or particle beam and removing the degraded compound and the unaffected compound from the substrate.

Alternatively, the method of the present invention may be used to manufacture a photomask which is then subsequently used in lithography to manufacture integrated circuits. In this embodiment the substrate should be translucent or transparent and the deposit formed by degradation of the compound should be opaque. The deposit provides a barrier to passage of ultraviolet light during use of the photomask in making integrated circuits, as with the chromium in conventional photomasks.

Thus in a yet further aspect, the present invention provides a method of manufacture of a photomask, said method comprising applying to a transparent or translucent substrate a compound which degrades under the effect of a radiant or particle beam to produce an opaque deposit, applying to selected surface areas of said compound such a radiant or particle beam and removing the degraded compound and the unaffected compound from the substrate.

In this embodiment the deposit formed by the action of the particle or radiant beam need only be opaque and there is no requirement for the deposit to be conductive. Therefore the deposit may be of any suitable opaque material, whether metal or non-metal. The opaque deposit may be for example a metal or semi-metal such as gold, tin, germanium or chromium, an alloy, or a non-metal such as silicon or carbon.

In the present invention, the compound may be heat-sensitive so that the use of a radiant beam in the form of a laser beam degrades the compound to produce the deposit.

Preferably, however, the particle beam is an electron beam, in which case the compound may be for example an organometallic compound which degrades under the effect of the beam to deposit a metal on the substrate.

Conventionally the steric properties of the organometallic material which may be used as the compound in the process of invention are optimised by selecting $d^8$ configurations which give square planar geometry in the organometallic compound. Such compounds include organometallic gold, platinum or palladium fluorides.

In a yet further aspect, the present invention provides a gold organometallic fluoride. Optionally the gold organometallic fluoride may be used in the method of deposition described herein.

Gold is an especially useful metal for inclusion in an organometallic compound to be used in the method of this invention, and a suitable organometallic form is di-sec butylaurum (III) fluoride dimer.

Gold chemistry exists mainly in the Au(I) and Au(III) oxidation states. Inorganic gold compounds usually have the linear 2 co-ordination state and occasionally exist in trigonal planar or tetrahedral configurations.

Au(III) compounds are in general square planar but can exist in five or six coordinated states. Simple organogold compounds (AuR—where R is any organic group) have not as yet been found although adduct compounds of Au(I) with phosphines or isocyanides are known. Trigonal planar Au(I) organoaurates (eg Li[AuCH$_3$]$_2$) exhibit low stability, spontaneously decomposing by reductive elimination of the methyl groups to give ethane. The trigonal planar gold complexes gain stability if complexed with larger ligands (eg Li(PMDT)[AuCH$_3$]$_2$, where PMDT=pentamethyl-diethylenetrisamine)

Au(I) organyls are also accessible through carbene insertion into the Au—Cl bond.

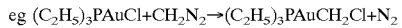

eg $(C_2H_5)_3PAuCl+CH_2N_2 \rightarrow (C_2H_5)_3PAuCH_2Cl+N_2$

Au(III) organyls also require additional ligation to provide stability. Square planar compounds are obtained eq: $(C_6F_5)_2AuClPPh_3$). Halogen bridging Au complexes are known through the auration reaction:

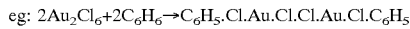

eg: $2Au_2Cl_6+2C_6H_6 \rightarrow C_6H_5.Cl.Au.Cl.Cl.Au.Cl.C_6H_5$

Other typical organometallic compounds for use in this invention are polyalkyl metal fluorides, for example polydibutyltin difluoride, as these compounds contain generally linear chains which allow good definition of the affected areas of the compound on application of the radiant or particle beam.

The organometallic compounds are advantageously fluorides since the fluoride component enhances the adhesion between the substrate (such as silicon or quartz) and the metal film formed after irradiation. The enhanced adhesive is believed to be due to the formation of Si—F bonds. This enhanced adhesion is not achieved with the equivalent chloride and bromide compounds. Particularly good adhesion is observed when tetra-sec-butyldiaurum difluoride is used as the organometallic compound. A further advantage is that an especially even dispersion of organometallic compound is observed where a fluoride compound is used.

Fluorine bridging in organogold complexes has not been reported but pentafluorochalchogenate derivatives of gold are known (ie Au(OTeF$_5$)$_3$). The group OTeF$_5$ is often regarded as a pseudohalogen but more precisely is a pseudofluorine. The ability of Au to form bridging species renders the gold pentafluorochalcogenate compound the only known binary transition metal derivative of OTeF$_5$. This compound is of a centrosymmetric dimer with four terminal TeF$_5$ groups and two u-oxo bridging bidentate OTeF$_5$ groups.

Further according to the invention there is provided a method of preparing polydibutyltin difluoride, comprising fluorinating polydibutyltin dichloride.

Polydibutyltin dichloride is commercially available but is unstable at ambient temperature. The difluoride, while known, has until now been very difficult to produce.

The fluorination may be carried out using for example sodium fluoride, and the resulting polydibutyltin difluoride may be used in the manufacture of photomasks by applying it, for example by spinning, to a transparent or translucent substrate such as quartz.

In this process the quartz is rapidly rotated while the polydibutyltin difluoride in solution is slowly applied, for example by drip, to it. The solvent is then driven off leaving an accurately-controlled layer of the organometallic compound.

In some cases it is possible to deposit the opaque material by application to the substrate of a solution of the degradable compound and then driving off the solvent, preferably by microwave heating which has the effect of allowing the solvent to be removed from the substrate interface early in the procedure, thereby producing effective adhesion between the deposited degradable compound and the substrate.

In investigating the yield of organometallic precursor material extracted from the reactant mixture as a function of solvent polarity, cyclohexane, n-hexane, isopentane, chlorofluorocarbon 113 (CCl$_2$FCClF$_2$), CFC-113a (CCl$_3$CF$_3$), n-pentane and iso-pentane have been examined. The optimum solvent to provide a smooth even distribution of organometallic material on a quartz substrate was found to be a low-boiling-point aliphatic hydrocarbon solvent. Hence, n-pentane or isopentane are excellent solvents for work to be performed at ambient temperatures.

Figure 1:
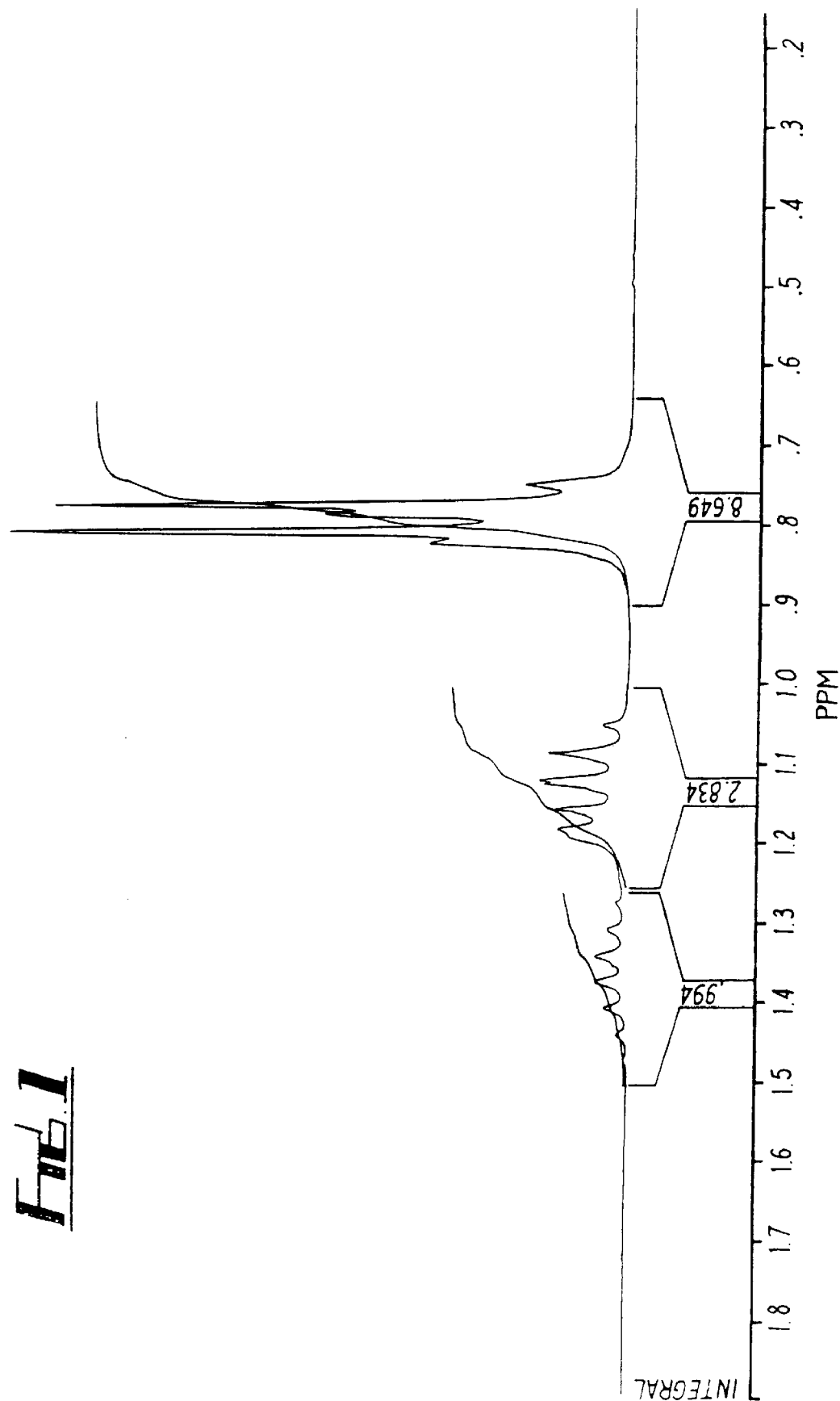
FIGS. 1 and 1a illustrate $^1$H NMR analysis of Di-sec butylarum (III) fluoride dimer.

Embodiments of the present invention will now be described by way of illustration in the following Examples.

EXAMPLE 1

Preparation of Polydibutyltin Difluoride

Analar grade methanol (50 ml, B.D.H.) was transferred to a conical flask containing 2.1 g of dried sodium fluoride (Aldrich Chemical Co.,). The flask was shaken to dissolve the solid material. Dibutyltin dichloride (0.5 g, Aldrich Chemical Co.,) was added and the conical flask was stoppered and sealed using paraffin film. The system was shaken for 1 hour, then allowed to stand for 12 hours at ambient temperature.

The reaction mixture was then passed through a sintered glass filter to remove any undissolved sodium fluoride prior to the eluent being transferred to a phase separation vessel. Petroleum ether (bp. 60°–80° C., 100 ml) was added to the eluent phase and the reaction mixture shaken before allowing the mixture to settle and separate. Using the upper phase, the purification process was repeated a further three times using methanol (100 ml) before the upper phase was finally transferred to a 250 ml round bottom flask. The flask containing the reaction solution was affixed to a rotary evaporator and allowed to evaporate down until a precipitate appeared.

The solution was analysed by Raman Spectroscopy and identified as a low molecular weight polymer of dibutyltin difluoride.

Application and Preparation of Organometallic Overlayer

The solution of polydibutyltin difluoride monomer prepared above was spun onto a clean polished quartz plate. As the solvent evaporated off a film of polymeric dibutyltin difluoride formed on the quartz substrate. The organometallic overlayer supported on the quartz substrate was placed in a JEOL T300 Scanning Electron Microscope and bombarded with electrons (energy 30 keV) for a time which varied from 5 s to 10 min over an area of 100×100 $\mu$m. of the organometallic sample, then moved to an adjacent area.

After irradiation of each area the sample was examined using an optical microscope to reveal a linear track of metallic particles, approx. 10 $\mu$m wide. The non-degraded polydibutyltin difluoride film was removed by dissolution in methanol.

Using the method of this embodiment it is possible to produce a photomask of very high definition so that dense and discrete patterns can be applied to silicon chips to provide integrated circuits. The method removes the need for affected electron beam resist to be dissolved as in the conventional method, and also for the wet etch process, both of which reduce the definition and performance of the photomask.

EXAMPLE 2

Preparation of Di-sec Butylaurum (III) Fluoride Dimer

Magnesium turnings were degreased by washing in sodium dried ether and transferred to a double-necked round bottom flask containing a magnetic stirring bar. Sufficient sodium dried ether was added to cover the magnesium turnings. The flask was fitted with a water cooled condenser and a dropping funnel charged with 5.62 g dibutyl bromide (Aldrich Chemical Co.) in 80 ml of sodium dried ether. The butylbromide/ether mixture was added slowly and allowed to react with stirring with the magnesium turnings. The system was left to react for 2 hours at ambient temperature.

The prepared butyl magnesium bromide/ether mixture was decanted to a dry dropping vessel and fitted to a double necked roundbottom flask containing an etheral solution of aurum (III) chloride (500 mg in 20 ml ether Aldrich Chemical Co) cooled with powdered ice. The etheral solution of butyl magnesium bromide was added slowly with stirring to the aurum (III) chloride solution over a 20 minute period. After reaction powdered ice was added to the reactant mixture which was then allowed to warm up to ambient temperature.

The resultant organometallic gold halide was extracted from the reactant mixture using isopentane in a phase separation process. A dry methanol/isopentane phase separation process was performed a further three times. The product mixture was reacted with sodium fluoride (Aldrich Chemical Co, 2.1 g) dissolved in 50ml of dried methanol (BDH), and shaken at ambient temperature over a 24 hour period. The mixture was then passed through a sintered glass filter to remove any undissolved NaF prior to the eluent being transferred to a phase separation vessel. Three phase separation cycles were performed using an isopentane/dry methanol mixture containing the reaction products, the hydrocarbon phase being carried over in each step of the separations. The final hydrocarbon phase was transferred to a round bottom flask, affixed to a rotary exaporator, and allowed to evaporate down until a precipitate appeared. The product material had a white waxy appearance and gave off a pungent odour. Contact of the product material with the skin left a purple stain consistent with the deposition of colloidal gold.

Characterisation of the product material was performed using $^1$H, $^{13}$C, $^{19}$F, and Distortionless Enhancement by Polarization Transfer (DEPT) liquid phase NMR (nuclear magnetic resonance) analysis using CDCl$_3$ or deuterobenzene as solvent (FIGS. 1–5). Mass spectroscopy was also used to identify the product material (FIGS. 6–7).

Figure 1A:
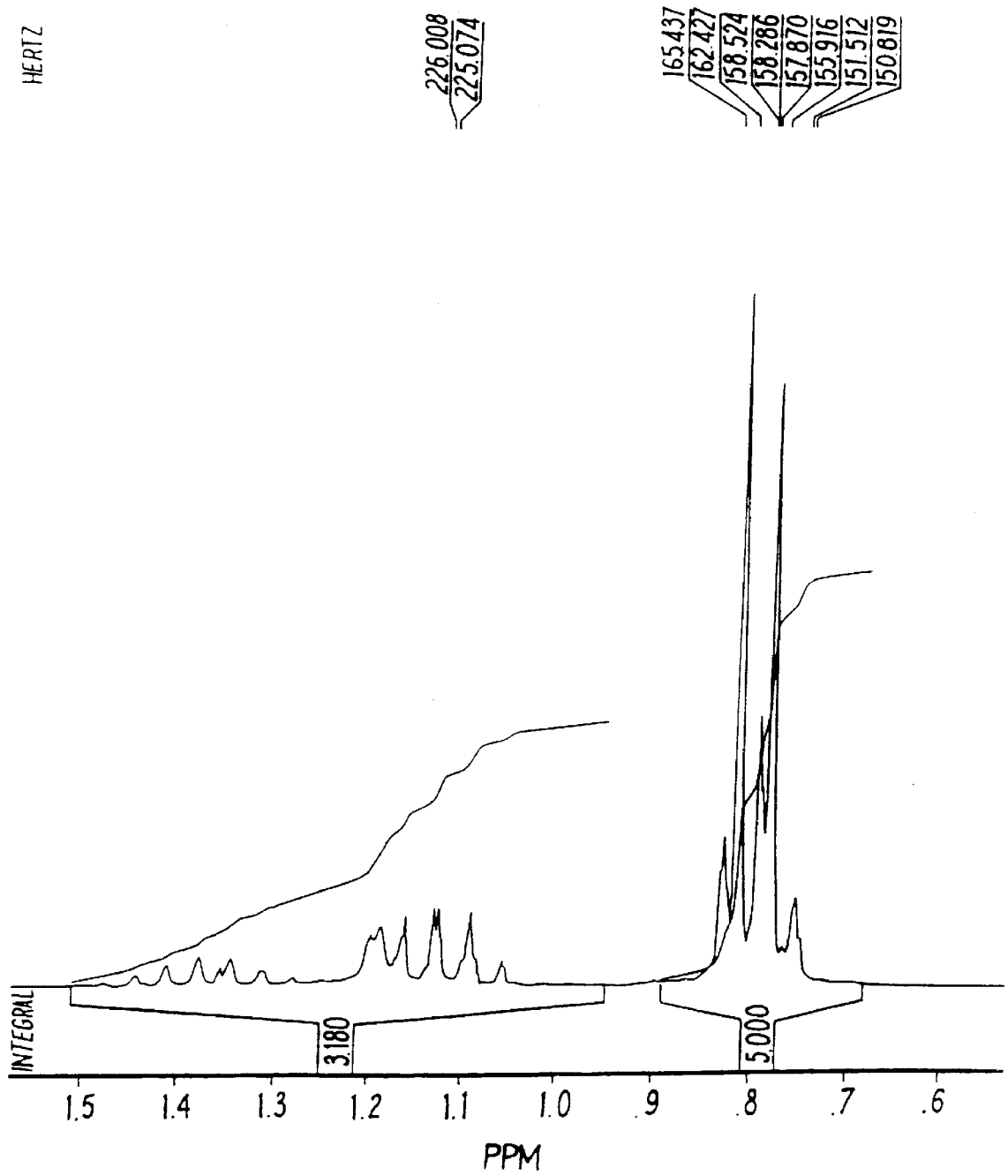
Figure 2:
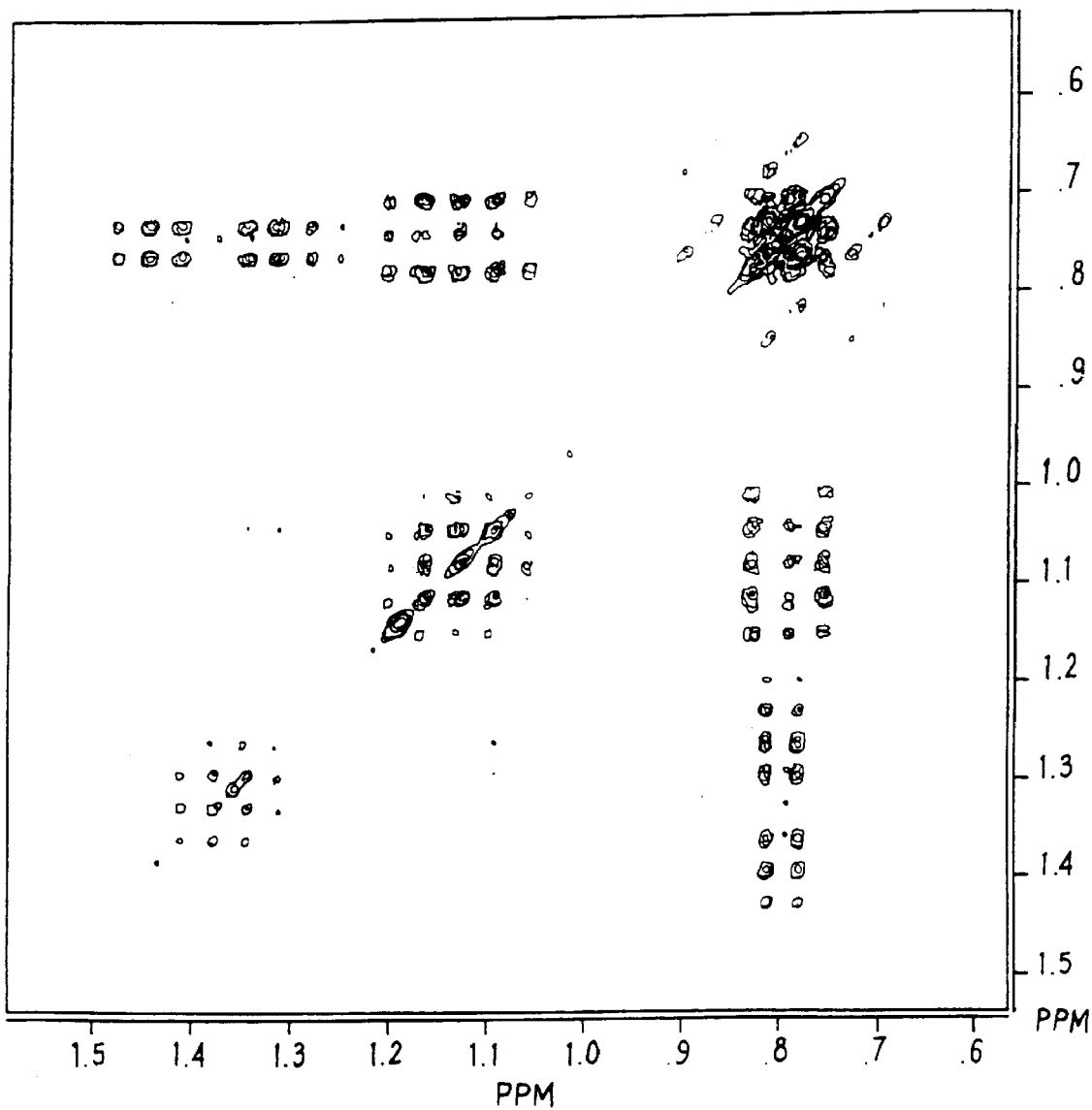
FIG. 2 illustrates two dimensional $^1$H analysis of Di-sec butylarum (III) fluoride dimer.
Figure 3:
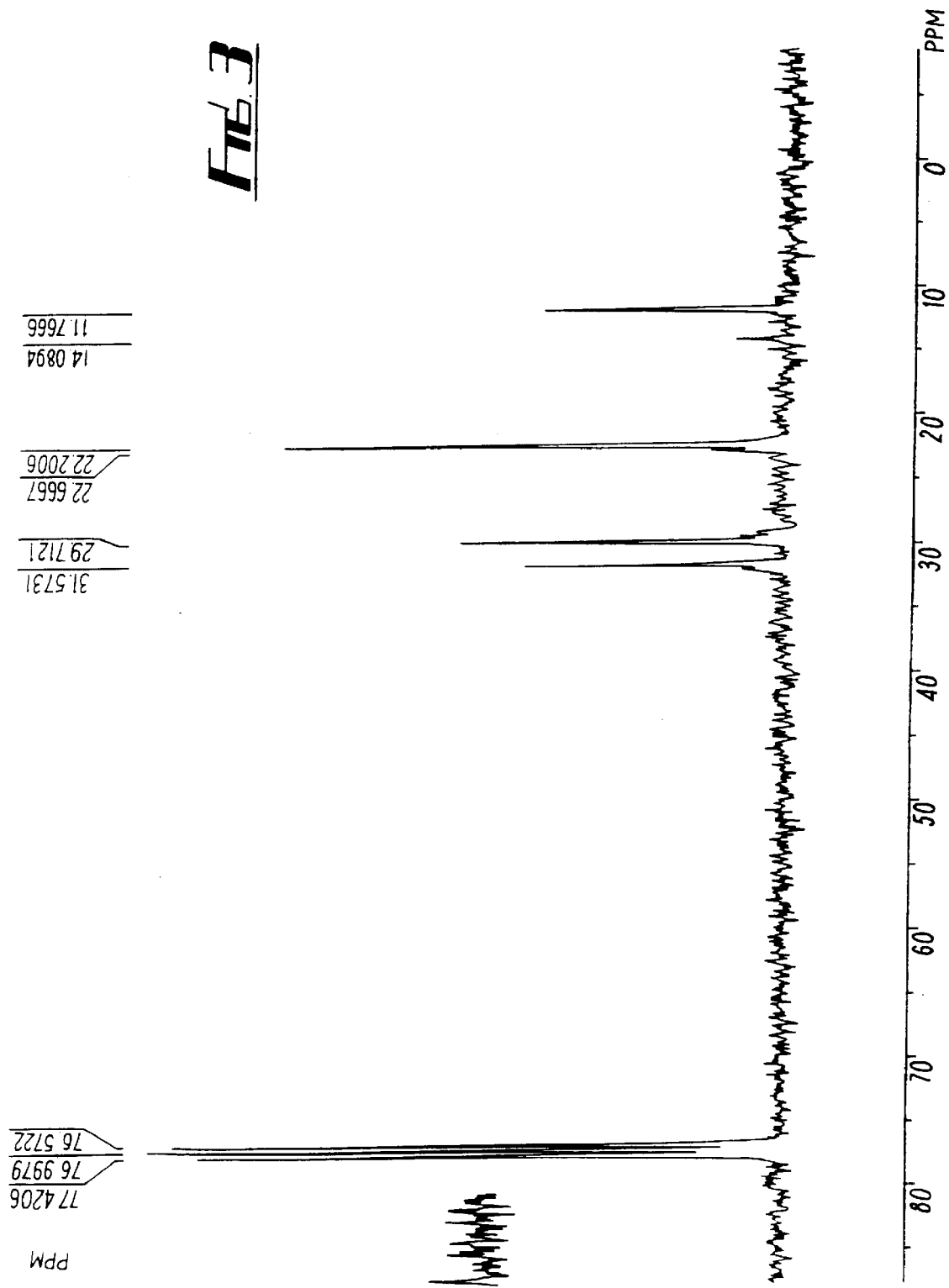
FIG. 3 illustrates $^{13}$C NMR analysis of Di-sec butylarum (III) fluoride dimer.
Figure 4:
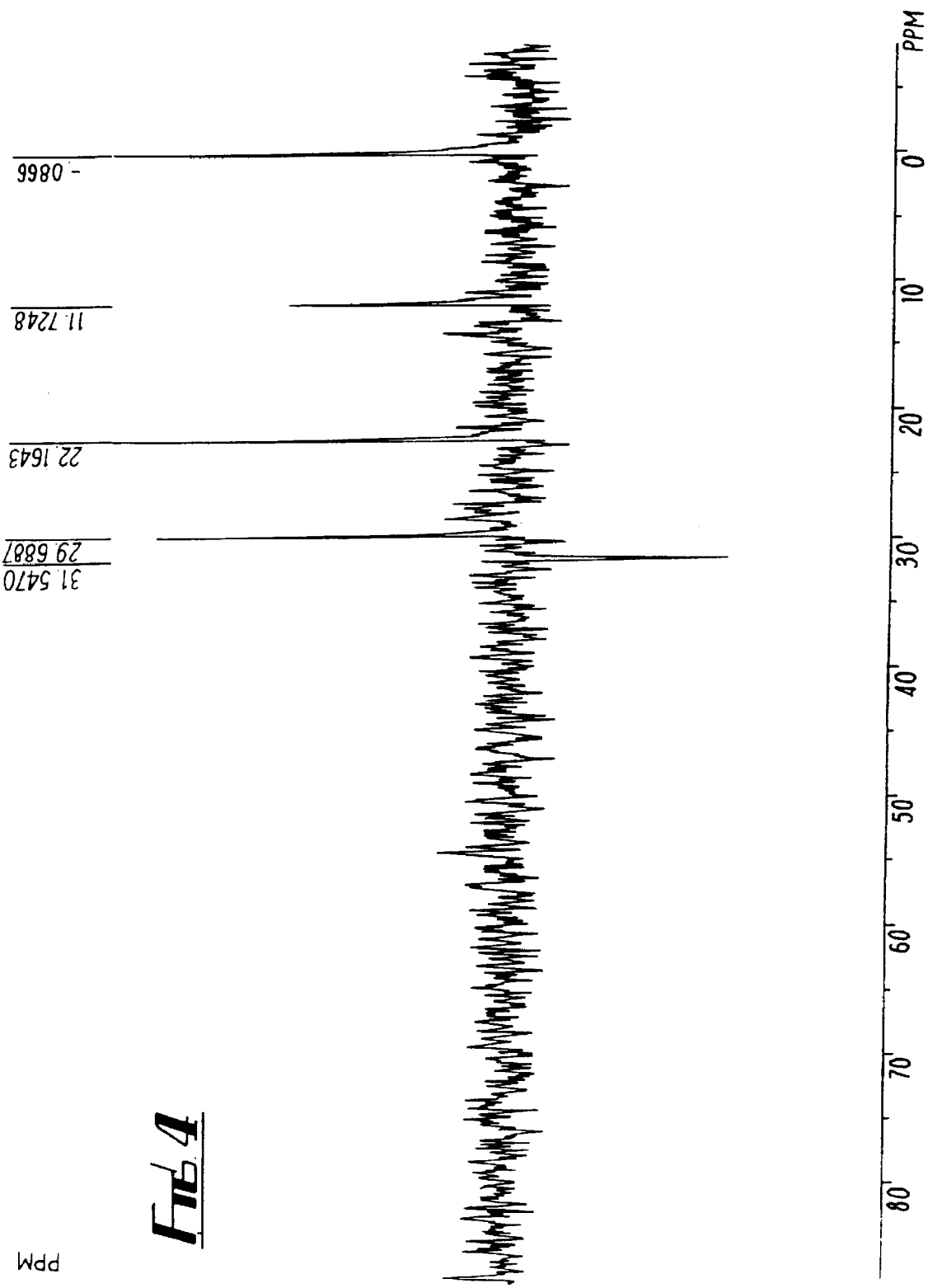
FIG. 4 illustrates DEPT analysis of Di-sec butylarum (III) fluoride dimer.
Figure 5:
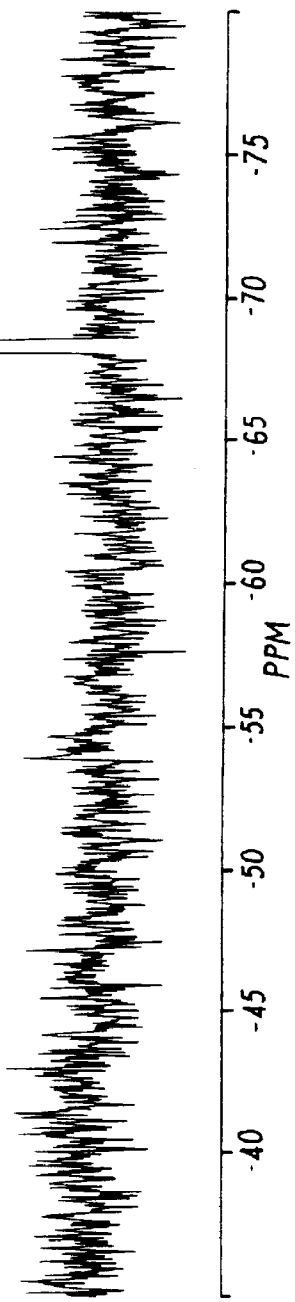
FIG. 5 illustrates $^{19}$F NMR analysis of Di-sec butylarum (III) fluoride dimer.

Results $^1$H NMR analysis of the product material gave peaks at 1.38 (hextet), 1.13 (hextet) and 0.79 (d of d) (FIGS. 1 and 1a). Two dimensional $^1$H analysis of the material shows three proton environments (FIG. 2) and DEPT analysis shows that the proton arrangement on the organic liquid is one carbon containing an even number of protons and three carbons containing an odd number of protons (FIG. 4). $^{13}$C NMR analysis (FIG. 3) of the product material shows 4 peaks at 31.5, 29.7, 22.2, 11.7 ppm relative to TMS. The data indicates that four carbon environments are present in the product material. $^{19}$F NMR analysis of the product material (proton coupled and proton decoupled spectra) shows a singlet peak at −66.3 ppm confirming the presence of fluorine in the product. The $^{19}$F NMR datum (FIG. 5) also indicates that the fluorine environment is contained in a symmetrical field.

Figure 6:
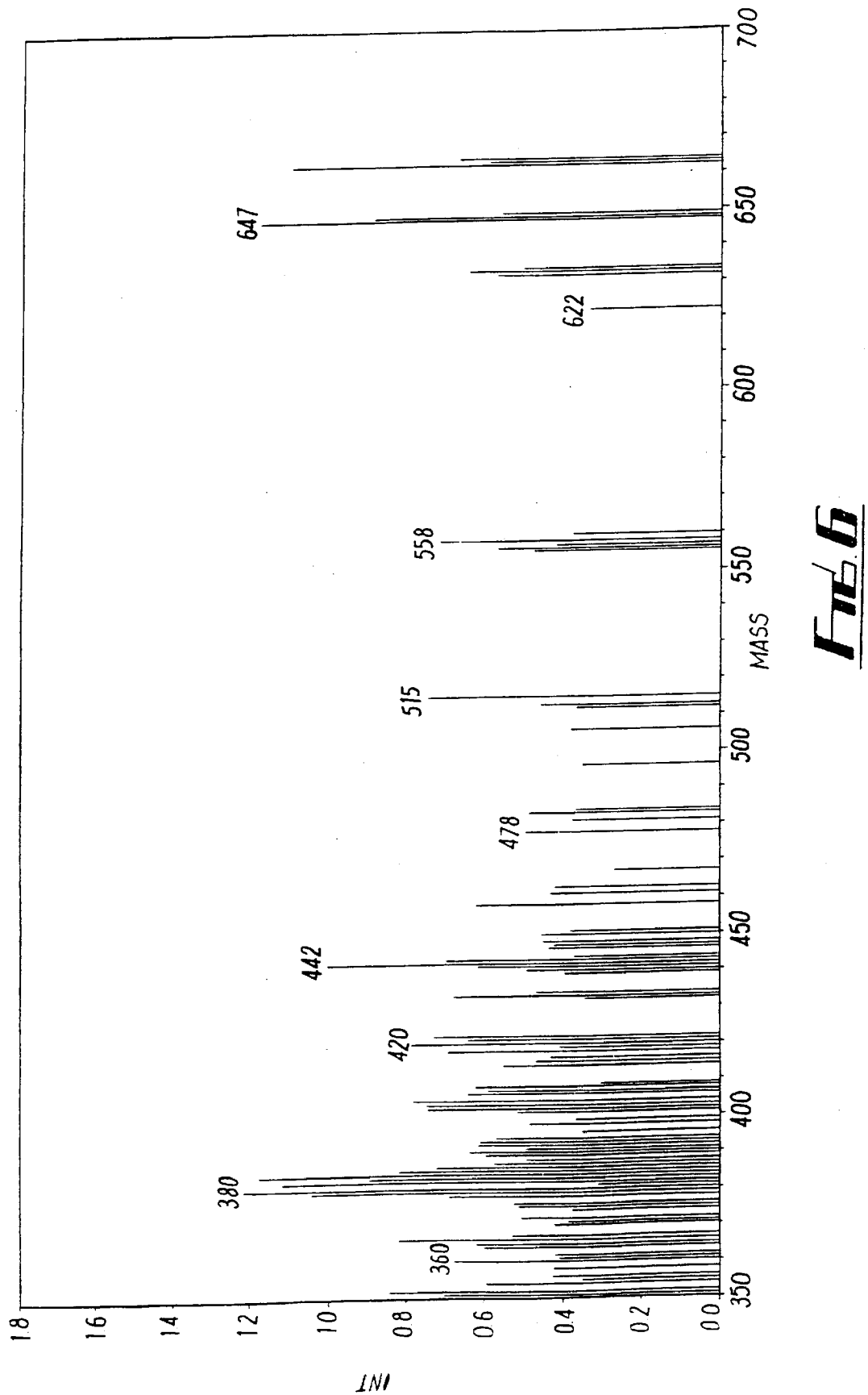
FIGS. 6 and 6a illustrate mass spectroscopic analysis of Di-sec butylarum (III) fluoride dimer.
Figure 6A:
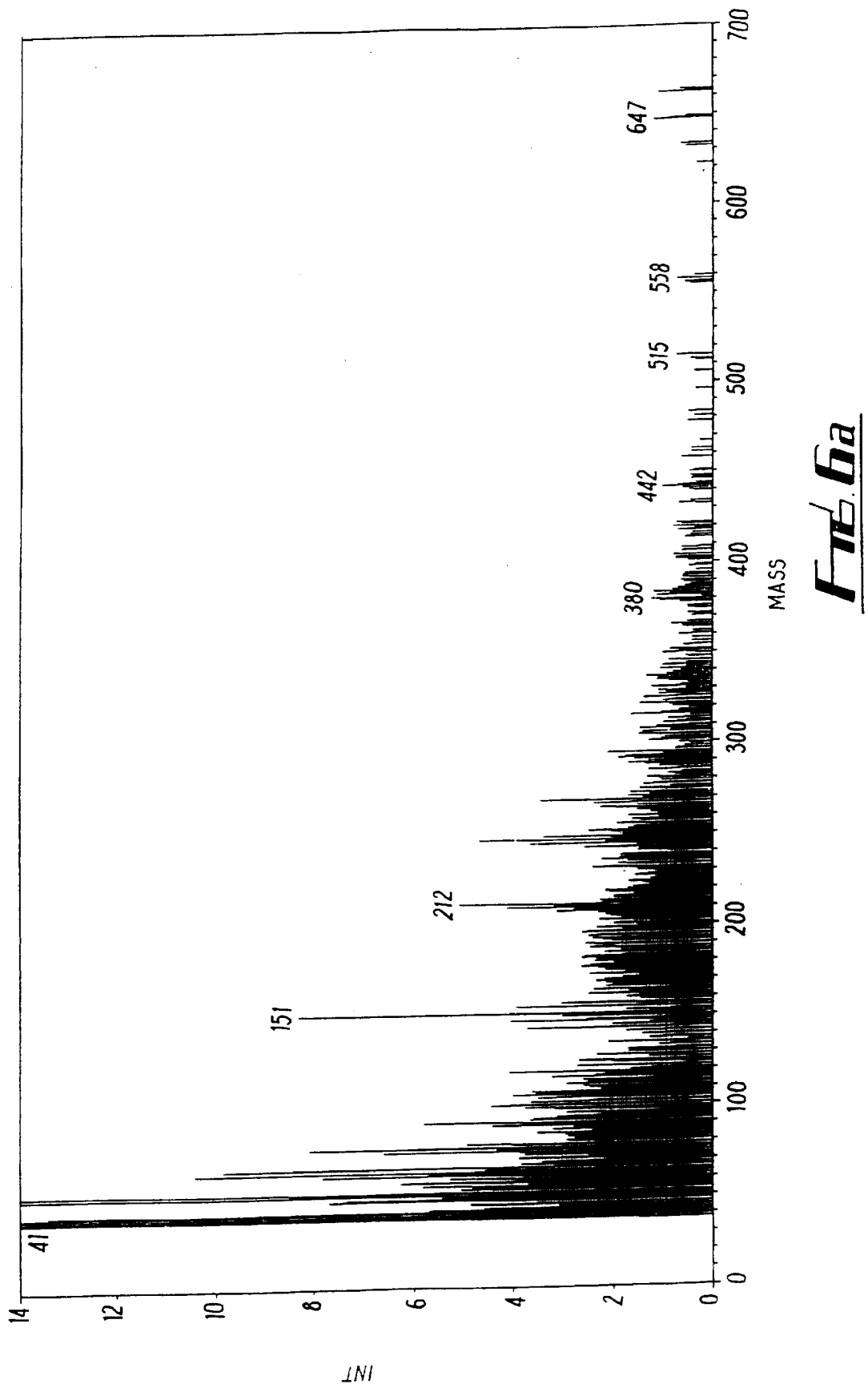
Figure 7:
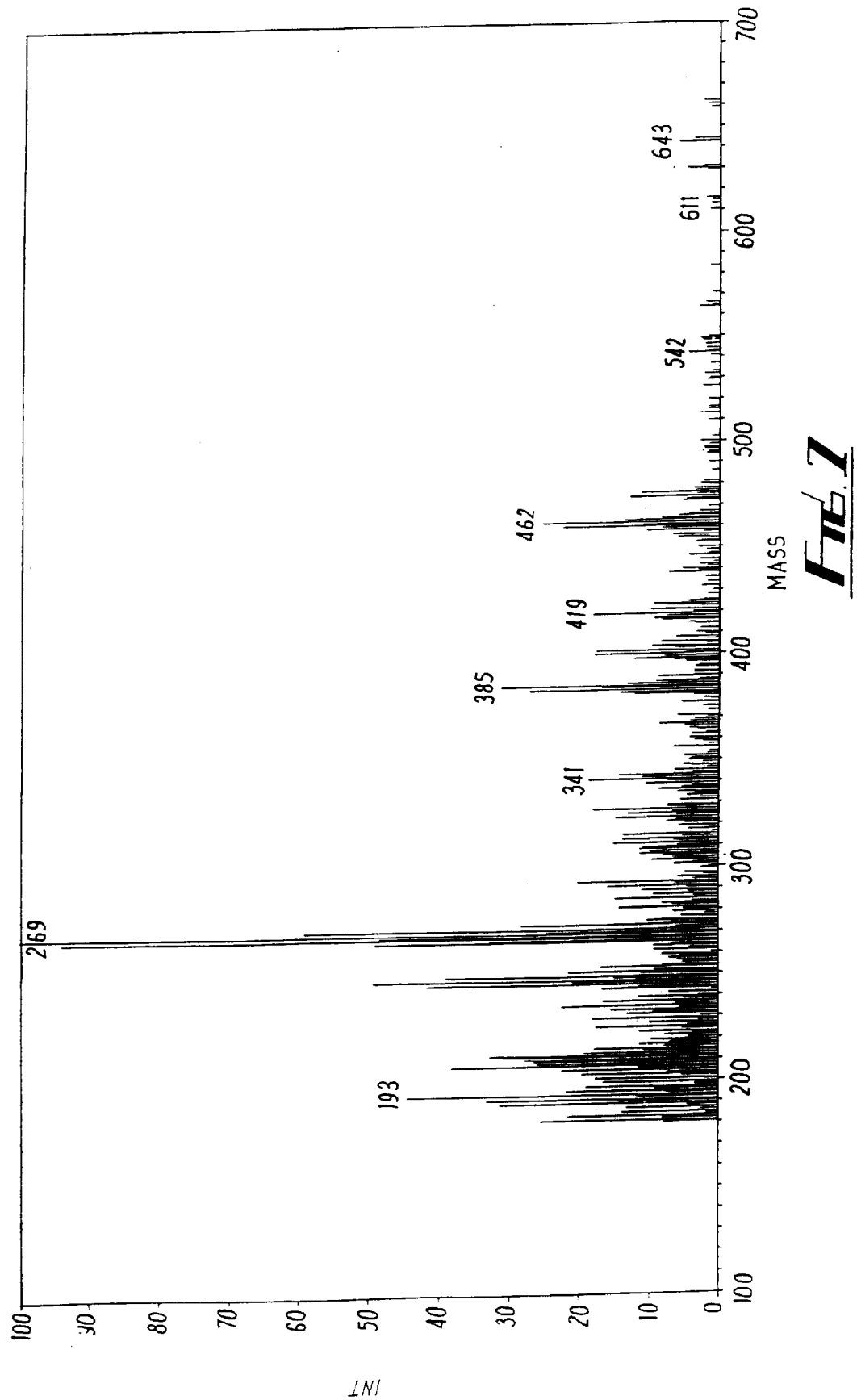
FIGS. 7 and 7a illustrate mass spectroscopic analysis of Di-sec butylarum (III) fluoride dimer.
Figure 7A:
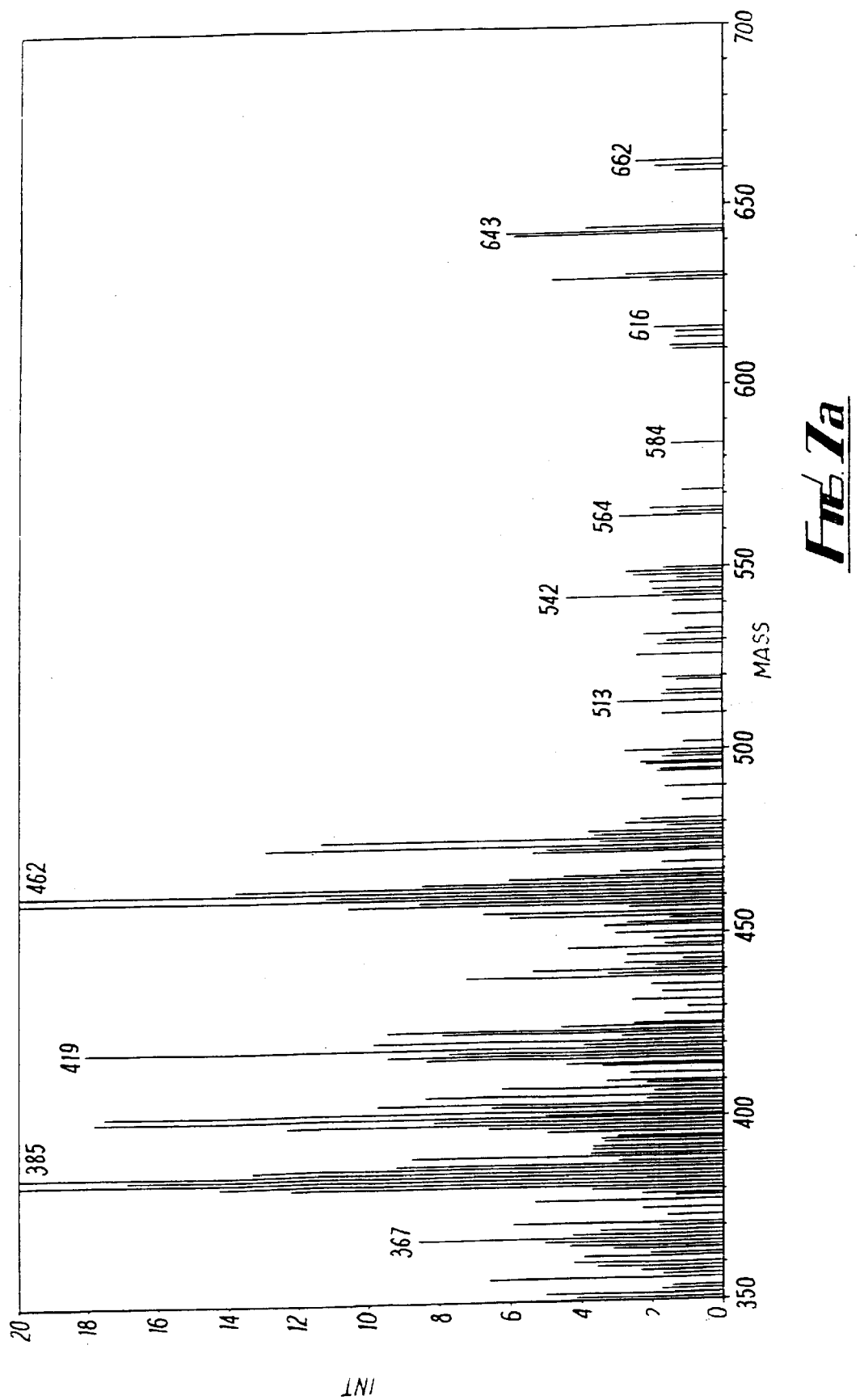

Mass spectroscopic analysis of the product material confirms the molecular ion mass of the product material to be 661 amu (FIGS. 6 and 7). Fragmentation of the product material is consistent with the loss of the following molecular fragments:

| Fragments | Residual Mass (amu) |
|---|---|
| CH$_3$— group | 647 |
| 2 @ CH— | 632 |
| 3 @ CH$_3$— + 1 @ C$_4$H$_9$— | 558 |
| 3 @ CH$_3$— + 1 @ C$_3$H$_7$— + 1 @ C$_4$H$_9$— | 516 |
| 1 @ Au | 463 |
| 1 @ Au + 1 @ C$_3$H$_7$— | 421 |
| 1 @ Au + 1 @ C$_3$H$_7$— + 1 @ F | 402 |
| 1 @ Au + 1 @ C$_4$H$_9$— + 1 @ F | 385 |
| 1 @ Au + 1 @ C$_4$H$_9$— + 2 @ F | 368 |
| 1 @ Au + 2 @ C$_4$H$_9$— + 1 @ C$_3$H$_7$— + 2 @ F | 269 |

UV analysis of an evaporated film of organoaurum product supported on quartz shows that the material is uv transparent in the range 900 nm–350 nm and hence the material is suited for use in mask-making where uv lithography is to be applied.

Studies have shown that the optimum solvent to be used, both in the abstraction of the product material from the phase separation stage of the preparation and in the deposition of the material onto a quartz substrate, is a low boiling point saturated alkane. Hence, the product material was applied to the quartz substrate using isopentane solvent.

The adhesion of organoaurum film to the quartz substrate material is enhanced by exposing the coated quartz substrate to microwave radiation prior to electron beam bombardment. It is thought that this process effectively evaporates off residual solvent—trapped between the organoaurum film and the quartz substrate to give better contact at the interface. The quartz substrate can also be coated with the organoaurum material via organometallic vapour deposition technique (OMVD). The OMVD deposition method results in a smoother more uniform coverage of the organoaurum material compared to the solvent application method.

Figure 8A:
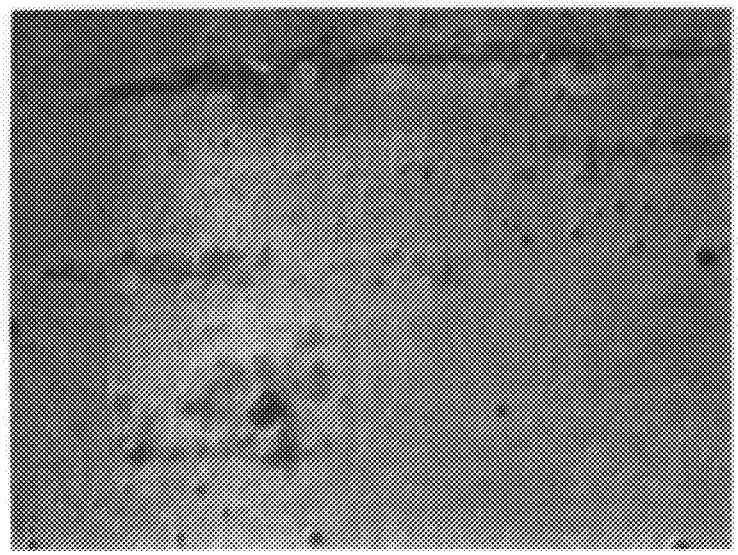
FIG. 8 illustrates organoaurum material reduced to metal component under electron beam irradiation.
Figure 8B:
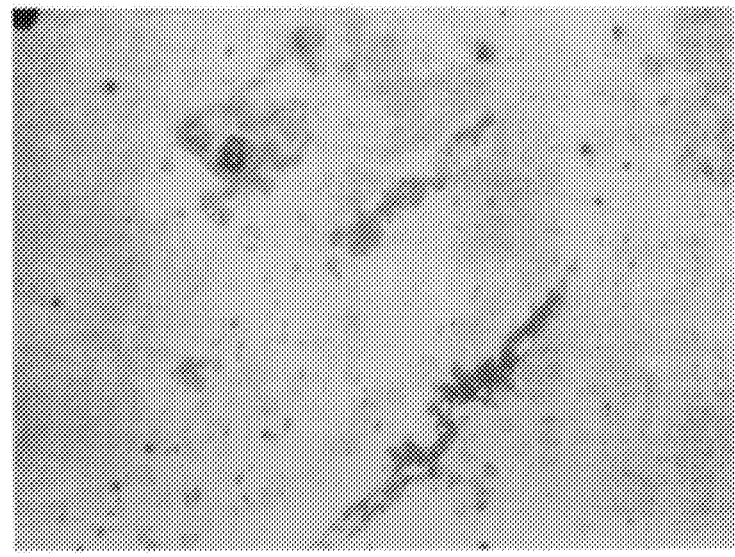

Electron beam bombardment of the coated quartz substrate was performed using a JEOL JSM-T220 Scanning Microscope. The microscope was set at an accelerating voltage of 20 kV, focusing and movement of the sample under the electron beam being both performed manually. The organoaurum material easily reduced to the metal component under the electron beam irradiation (FIG. 8). The best line width attained to date using the focussing power available on the JEOL instrument is 500 nm.

A sample of the dibutylaurum (III) bromide dimer was applied to the quartz substrate material and subjected to electron beam bombardment. A film of reduced gold metal was obtained on the quartz substrate.

Modifications and improvements can be made without departing from the scope of the invention, for example by using vapour phase deposition of the metal-containing polymer.

EXAMPLE 3
Preparation of Dibutylplatinum (IV) Fluoride Dimer

Magnesium turnings were degreased by washing in sodium dried ether and transferred to a double-necked round bottom flask containing a magnetic stirring bar. Sodium dried ether was added sufficient to cover the magnesium turnings. The flask was fitted with a water cooled condenser and a dropping funnel charged with 5.62 g dibutyl bromide (Aldrich Chemical Co.) in 80 ml of sodium dried ether. The butylbromide/ether mixture was added slowly and allowed to react with stirring with the magnesium turnings. The system was left to react for 2 hours at ambient temperature.

The prepared butylmagnesium bromide/ether mixture was decanted to a dry dropping vessel and fitted to a double necked round bottom flask containing 500 mg of platinum (IV) chloride (Aldrich Chemical Co) cooled with powdered ice. The butylmagnesium bromide mixture was added slowly with stirring to the platinum (IV) chloride solution. After reaction powdered ice was added to the reactant mixture and allowed to warm up to ambient temperature.

The dibutylplatinum bromide diner was extracted from the reactant mixture using n-pentane in a phase separation process. A dry methanol/n-pentane phase separation process was performed a further three times. The product mixture was reacted with sodium fluoride in dry methanol as described for the polydibutyltin difluoride process.

The dibutylplatinum (IV) fluoride dimer product was applied to a clean quartz substrate from an n-pentane solution and n-pentane was driven off in a microwave cooker to bake the product onto the quartz. The microwave process ensured that the n-pentane was driven off from the quartz interface instead of from its own surface. This gave very good deposition of the product on the quartz and allowed very good definition after electron beam bombardment. A film of reduced platinum metal was obtained supported on the quartz substrate.

A sample of the dibutylplatinum (IV) bromide dimer was applied to the quartz substrate material and subjected to electron beam bombardment. A film of reduced platinum metal was obtained on the quartz substrate.

Figure 9:
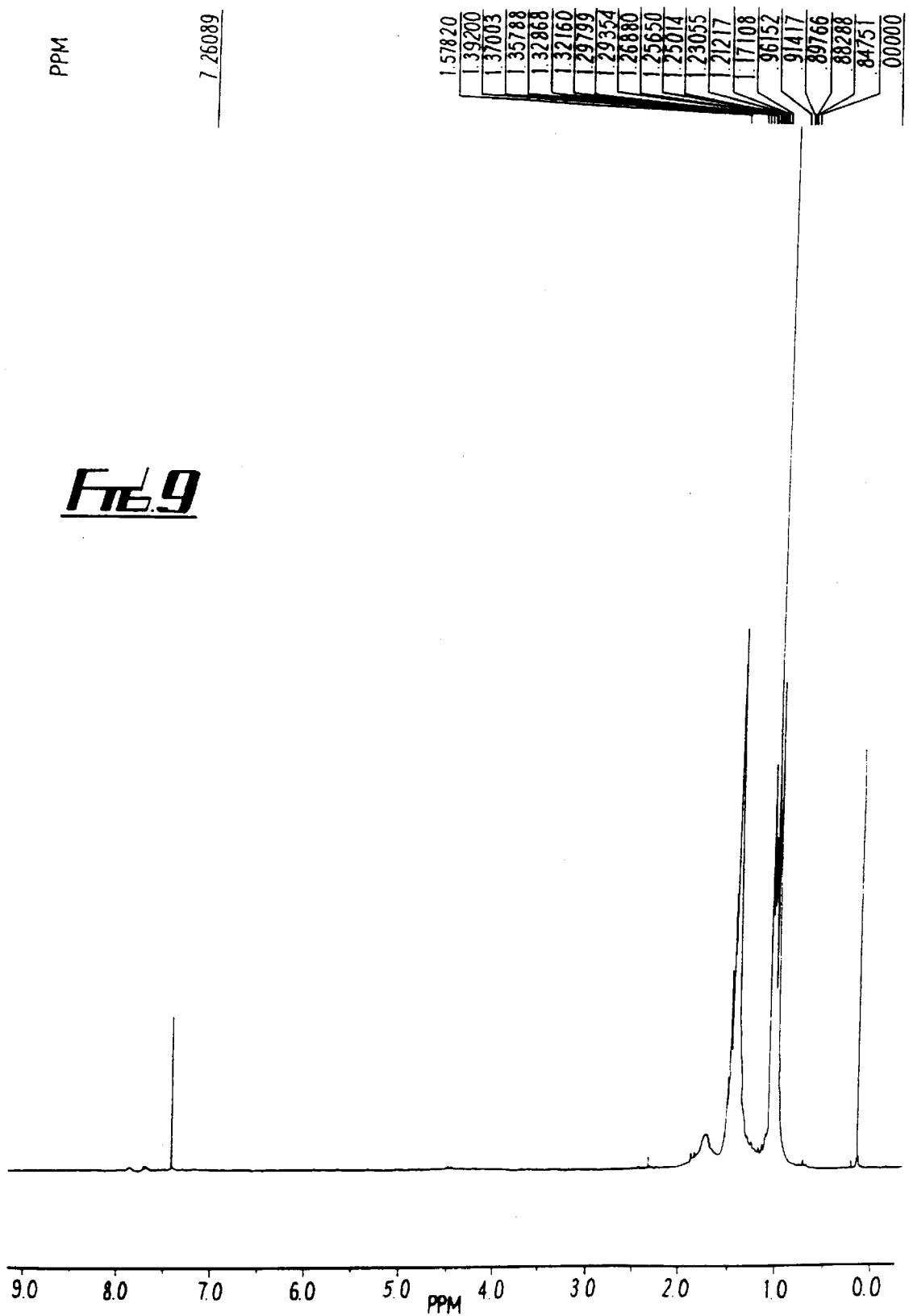
FIG. 9 illustrates $^1$H NMR analysis of propyl auric halide material.
Figure 10:
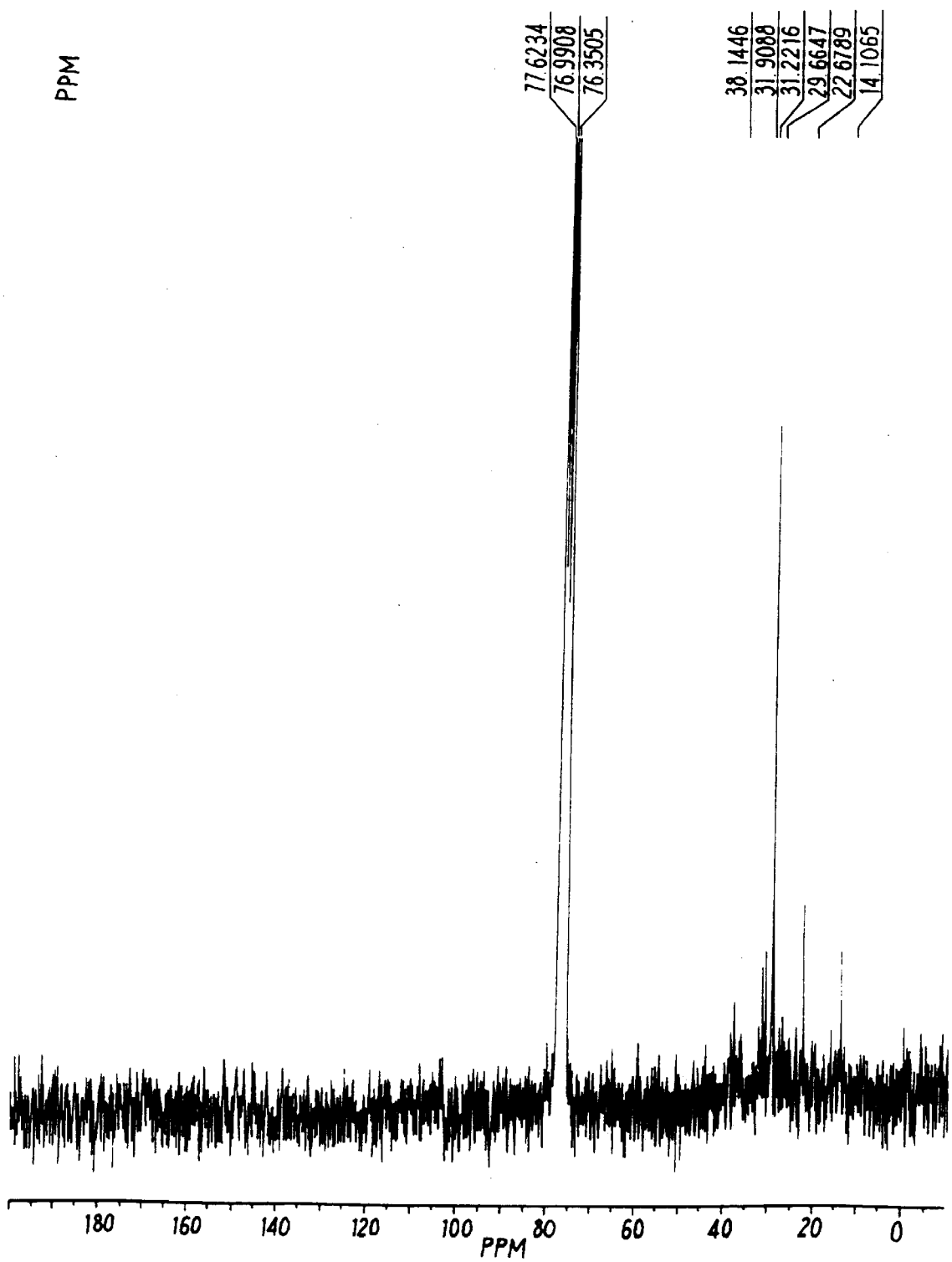
FIG. 10 illustrates $^{13}$C NMR analysis of propyl auric halide material.

EXAMPLES 4–7
Preparation of Propyl, Tertiary butyl, cyclohexylmethyl, benzyl analogues An analogous procedure to that described in Example 2 was performed to prepare the propyl, tertiary butyl, cyclohexylmethyl and benzyl analogues of organo gold halides. The preparation of the organo magnesium halide intermediate involved reaction of degreased magnesium turnings with the ethernal solutions of the appropriate propyl, tertiary butyl, cyclohexylmethyl and benzyl bromides respectively.
Results
  a) NMR analysis of the Propyl Auric Halide Material
    The $^1$H NMR of the product material from the reaction of the propyl magnesium Grinard with an ethernal solution of auric (III) chloride is shown in FIG. 9. The NMR shows peaks at 0.89 ppm (triplet), and 1.29 ppm (multiplet) relative to TMS (tetramethylsilane), which is consistent with the spectrum expected from the propyl ligand. The broad band at 1.57 ppm is consistent with that expected for the —CH$_2$— adjacent to a group inducing electron shielding. The $^{13}$C NMR is shown in FIG. 10. Although noisy, the spectrum shows three peaks at 14 ppm, 22 ppm and 33 ppm relative to TMS. The $^{13}C$ environments are consistent with $CH_3$ —$CH_2$— and a shielded —$CH_2$— respectively. The $^{19}F$ NMR of the sample (proton coupled and decoupled) showed a singlet at −67.64 ppm relative to $CCl_3F$ indicating that the material contained fluorine in a symmetrical field.

The product material was applied to a quartz substrate as described in Example 2. Electron beam bombardment was applied to the coated quartz material as described in Example 2. The material reduced under the electron beam bombardment to give gold lines identical to those obtained from the tetrabutyl diaurum difluoride material.

b) NMR analysis of the Benzyl Auric Halide Material

Figure 11:
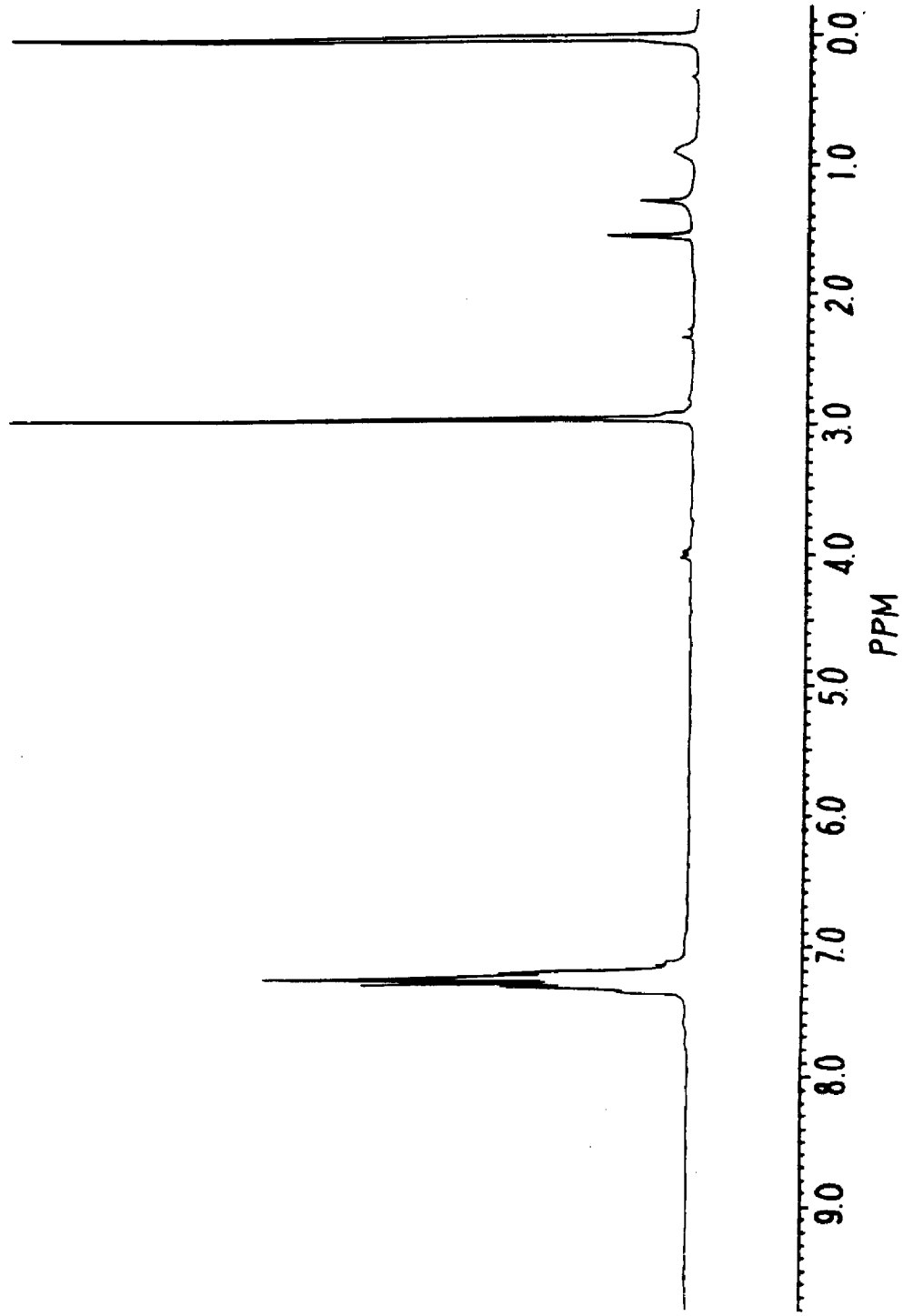
FIG. 11 illustrates the $^1$H NMR spectrum of benzyl auric halide material.
Figure 12:
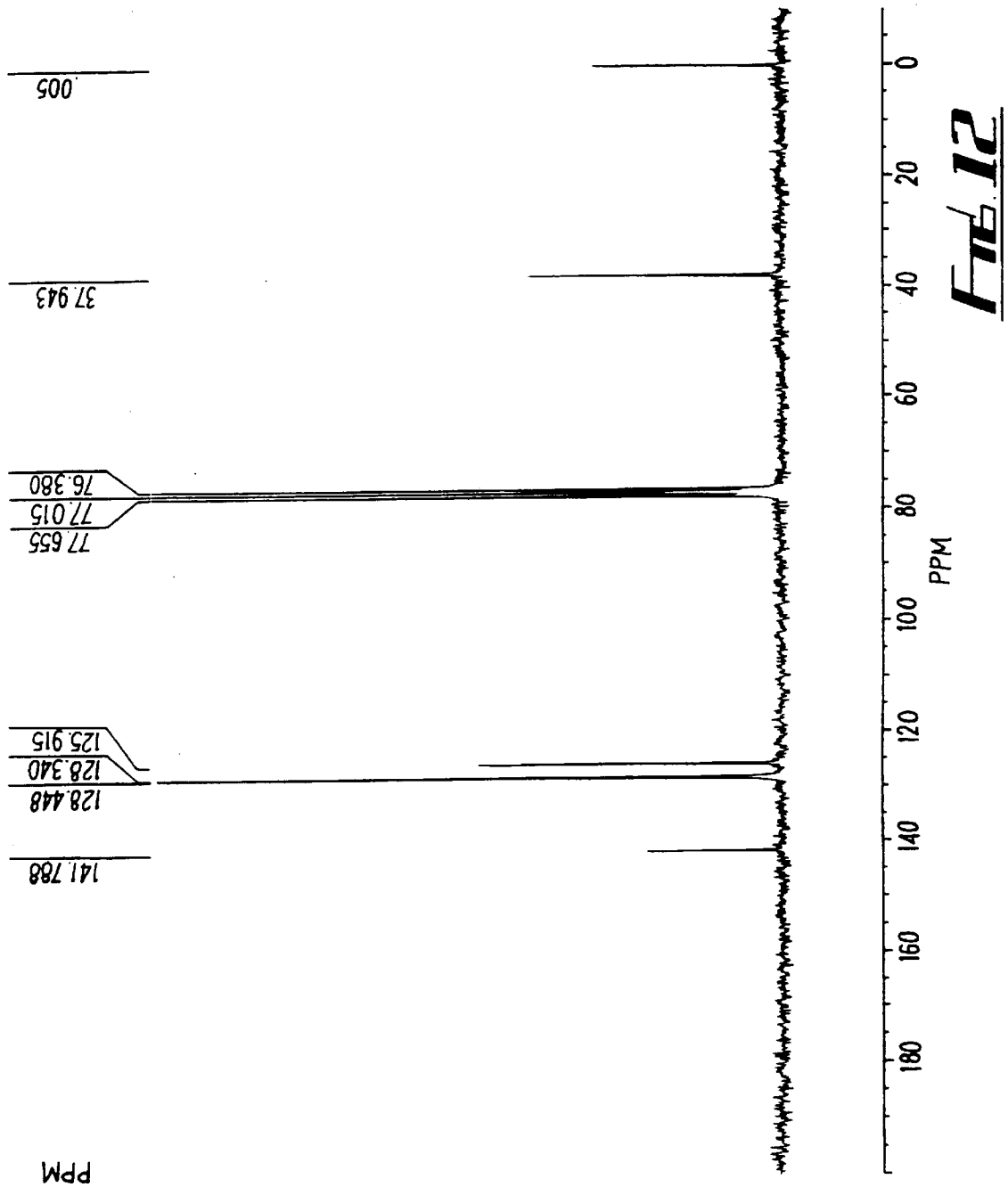
FIG. 12 illustrates the $^{13}$C spectrum of benzyl auric halide material.

The $^1H$ NMR spectrum of the product material is presented in FIG. 11. The NMR data shows major peaks at 7.3 ppm (multiplet) and 2.9 ppm (singlet) relative to TMS. Smaller peaks consistent with trace quantities of isopentane are also evident. The spectrum shows that the product material contains ligated benzyl groups. The $^{13}C$ spectrum is presented in FIG. 12. The spectrum shows peaks at 141.7 ppm, 128.5 ppm, 128.3 ppm, 125.9 ppm and 37.9 ppm relative to TMS. The $^{13}C$ environments are consistent with the distribution of shielding effect over the benzyl group ligated to an electron inducing species. The $^{19}F$ NMR showed a singlet at −67 ppm relative to CFC-11, similar to those obtained for the previous samples.

The product material from the benzyl Grinard reagent reaction with an etheral solution of auric (III) chloride was applied to a clean quartz substrate and subjected to electron beam bombardment as described in Example 2. The material did not reduce to give metal lines.

c) NMR Analysis of the t-Butyl Auric Halide Material

Figure 13:
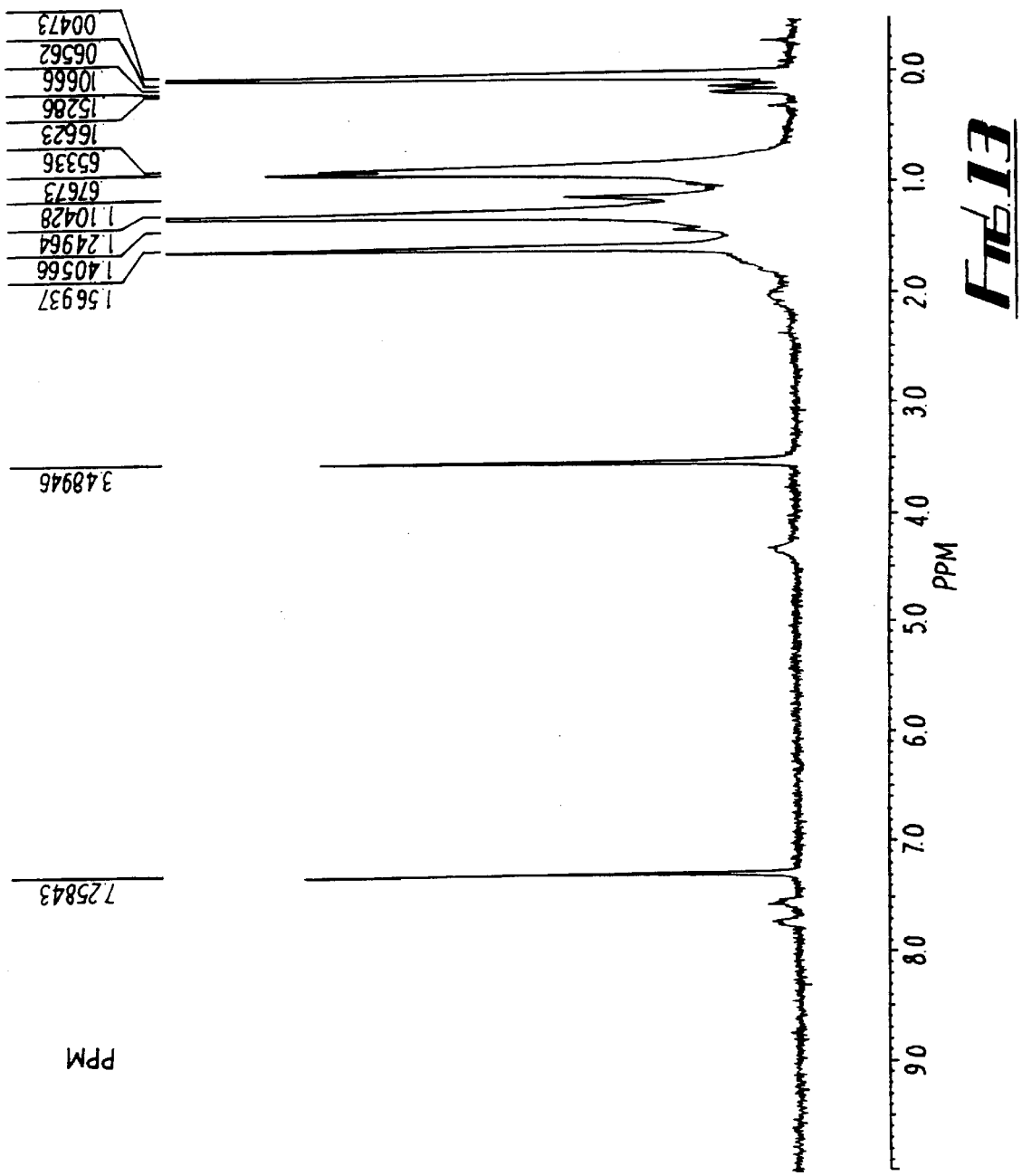
FIG. 13 illustrates the $^1$H NMR analysis of t-Butyl auric halide material.

The $^1H$ NMR analysis of the product material from the reaction of the t-butyl Grinard reagent with an etheral solution of auric (III) halide is presented in FIG. 13. The NMR data shows the presence of a major peak at 1.24 ppm (singlet) relative to TMS which is consistent with that expected for the t-butyl group. Impurities in the NMR have been identified to be MeOH, TMS and $CHCl_3$. Peaks consistent with some trace hydrocarbon solvent are also observed. The $^{19}F$ NMR analysis showed one peak at −67 ppm relative to CFC-11.

Figure 14:
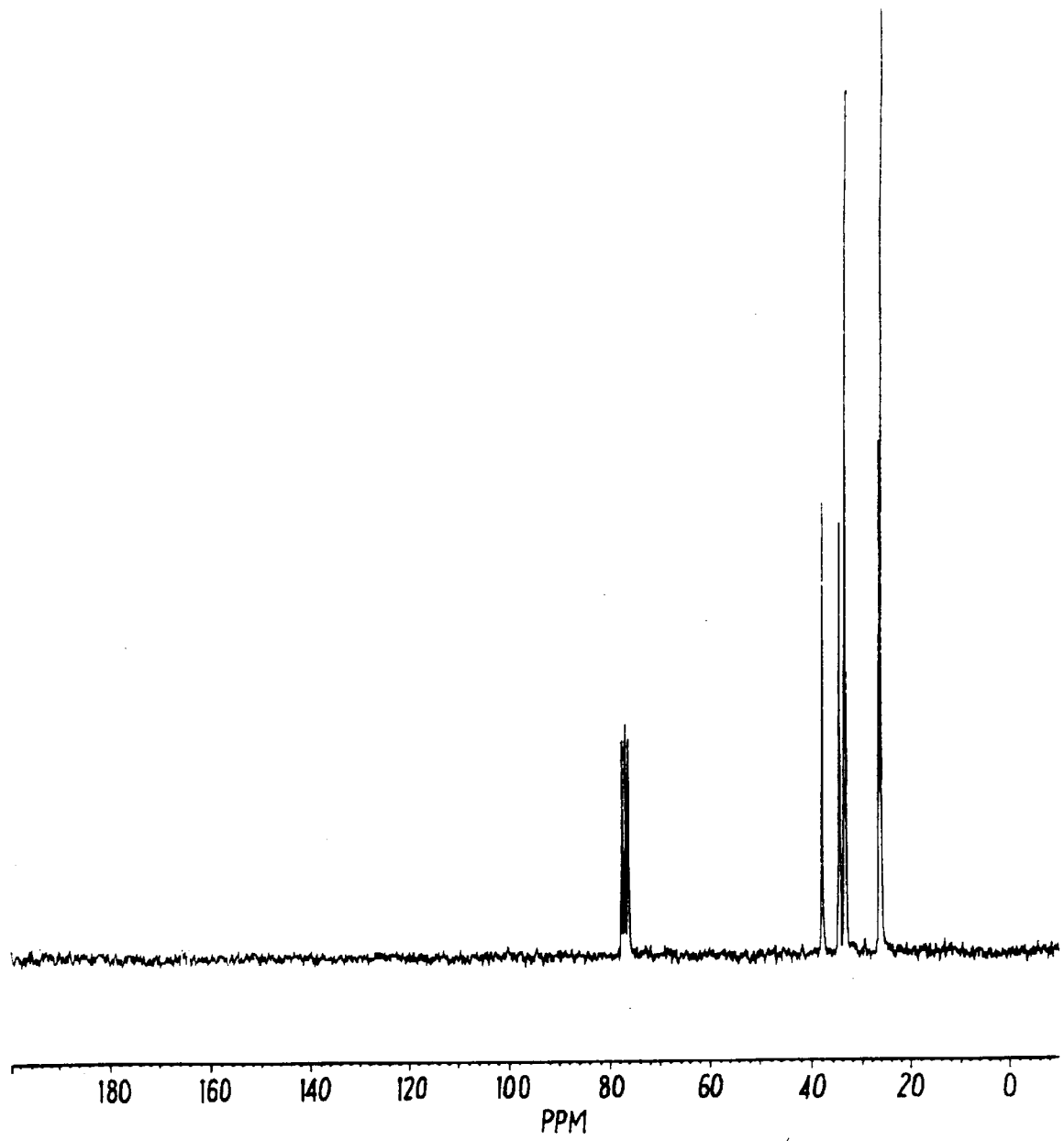
FIG. 14 shows $^{13}$C NMR spectrum of cyclohexylmethyl auric (III) material.
Figure 15:
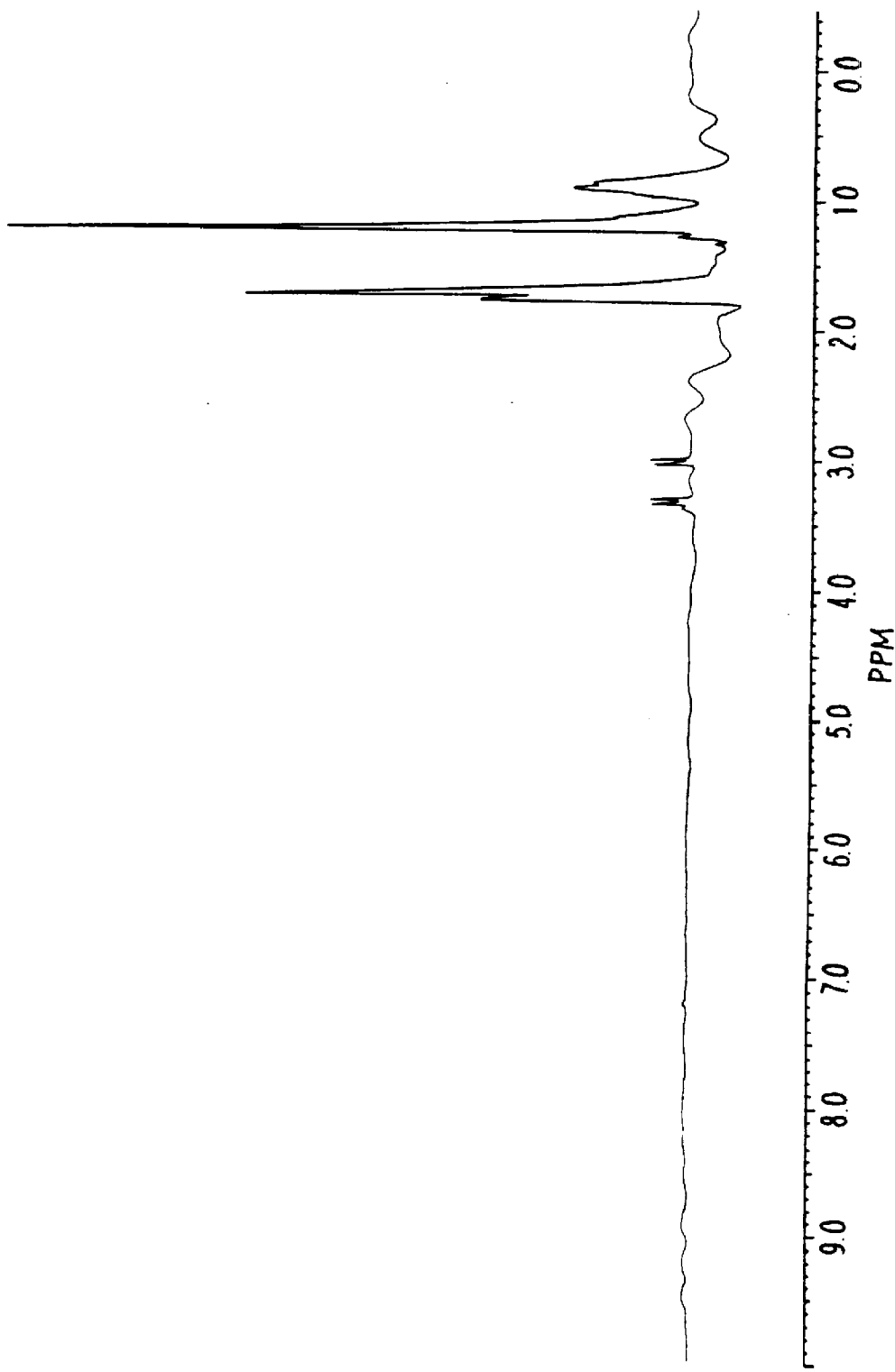
FIG. 15 illustrates $^1$H NMR analysis of cyclohexylemthyl auric (III) material.
Figure 16:
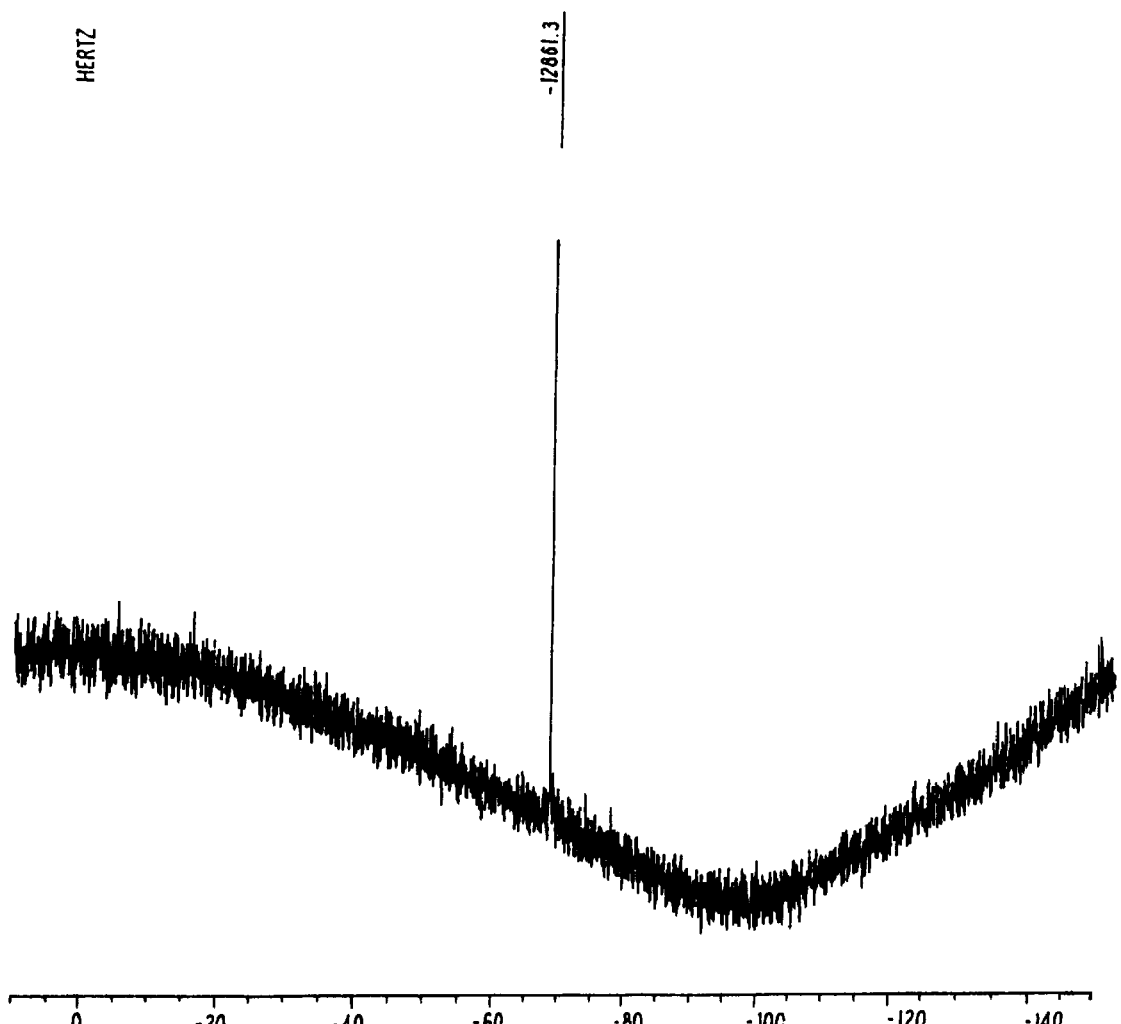
FIG. 16 illustrates $^{19}$F spectrum of cyclohexylmethyl auric (III) material.

The product material from the reaction was applied to a clean quartz substrate and subjected to electron beam bombardment as described in Example 2. The material did not reduce to give gold metal lines.

d) NMR Analysis of the Cyclohexylmethyl Auric (III) Material:

The $^{13}C$ NMR spectrum is presented in FIG. 14. The spectrum shows peaks at 36.15 ppm, 34.67 ppm, 33.6 ppm and a doublet at 26.6 ppm relative to TMS. The spectrum is consistent with that expected for methyl cyclohexane. The $^1H$ NMR analysis is presented in FIG. 15. The spectrum shows peaks at 1.2 ppm, (singlet) 1.6 and 1.7 ppm (singlets), 2.9 and 3.25 ppm (doublets). The spectrum is consistent with that of methylcyclohexane. The $^{19}F$ spectrum is shown in FIG. 16. A singlet peak at −68 ppm relative to CFC-11 is again observed.

The product material from the methylcyclohexyl aurum reaction was applied to a clean quartz substrate and subjected to electron beam bombardment as described in Example 2. The material did reduce under the conditions used to deposit fine lines of gold as observed under optical magnification. The width of the gold lines obtained were ca 500 nm.

EXAMPLE 8

Preparation of Organoplatinum Halide Complex

The preparation of platinum analogue materials was performed analogously to those described in Example 2. Propyl, butyl and methylcyclohexane analogues were prepared. The respective organomagnesium halide intermediate material was reacted with an etheral solution of platinum (IV) chloride (Johnson Matthey) at 0° C. Phase separation of the product material was performed as described in Example 2. The product material obtained had a white waxy appearance similar to that obtained from the gold complexes.

Results a) NMR Analysis of the Product Material from t-Butyl Platinum Fluoride

Figure 17:
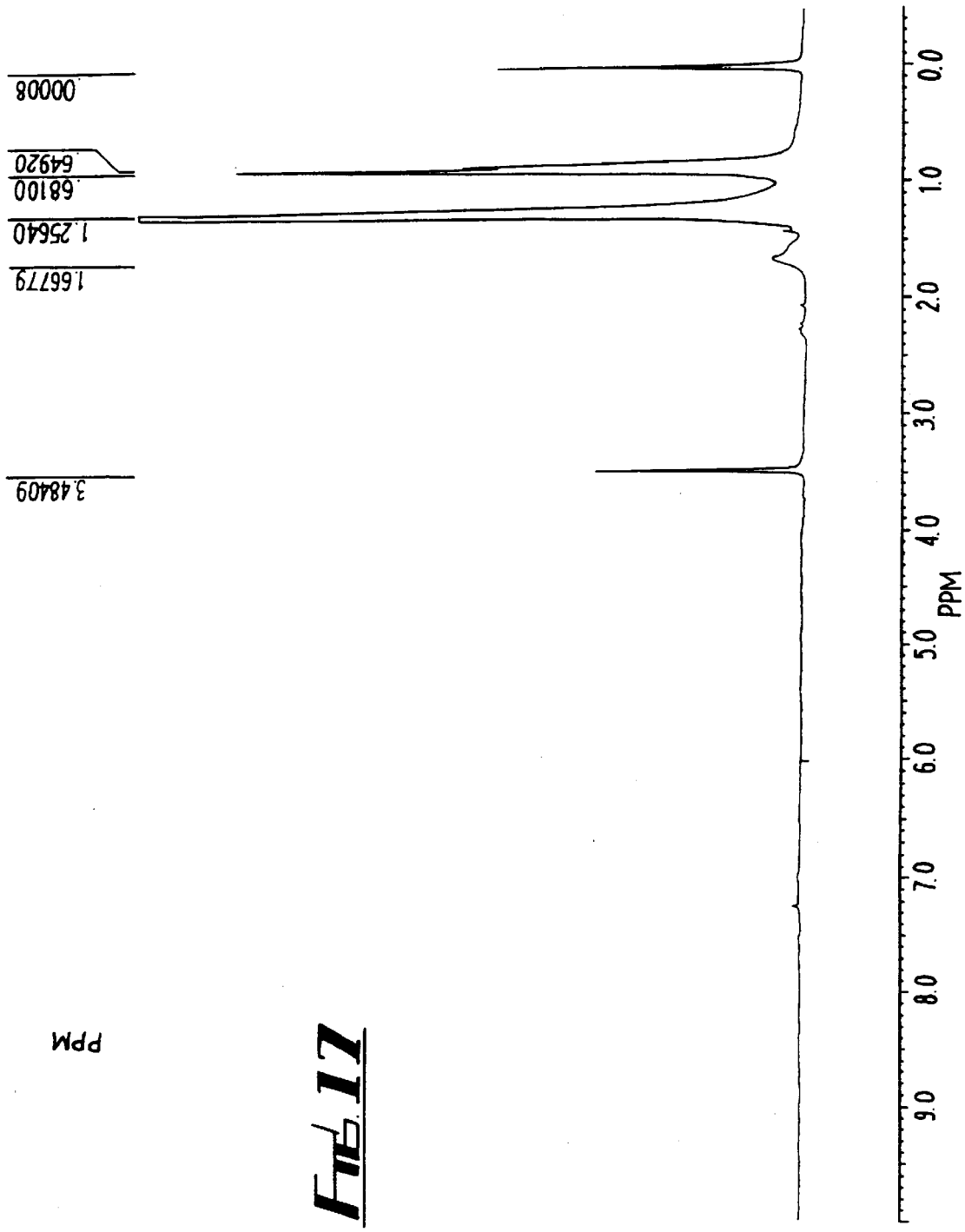
FIG. 17 illustrates $^1$H NMR analysis of product material from t-Butyl platinum fluoride.

The $^1H$ NMR analysis is presented in FIG. 17. The NMR shows the major peak at 1.25 ppm (singlet) with evidence of MeOH solvent in the sample. The $^{19}F$ NMR analysis gave one peak at −67.66 ppm.

b) NMR analysis of the Butyl platinic halide product

Figure 18:
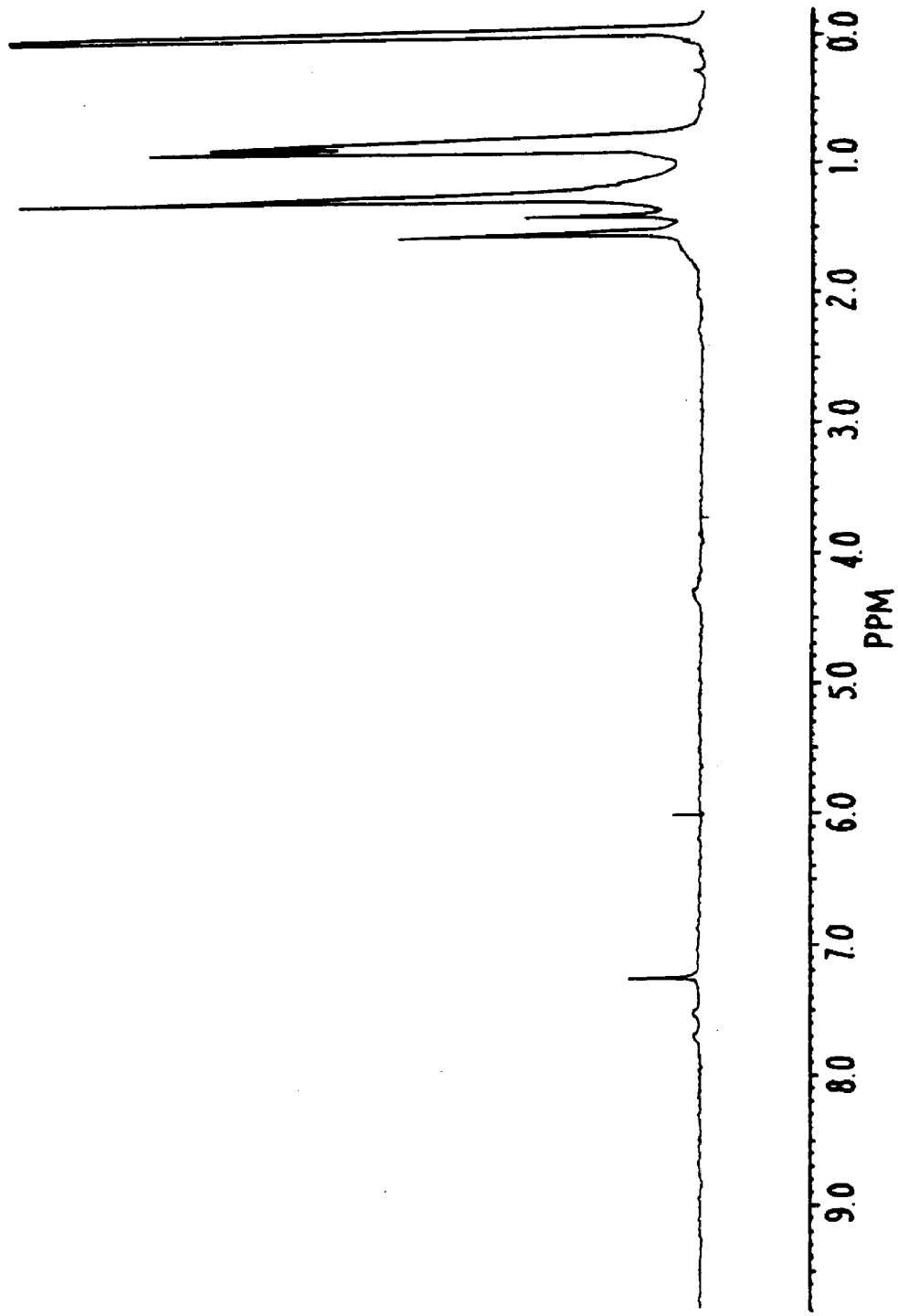
FIG. 18 illustrates $^1$H NMR analysis of Butyl platiric halide product.
Figure 19:
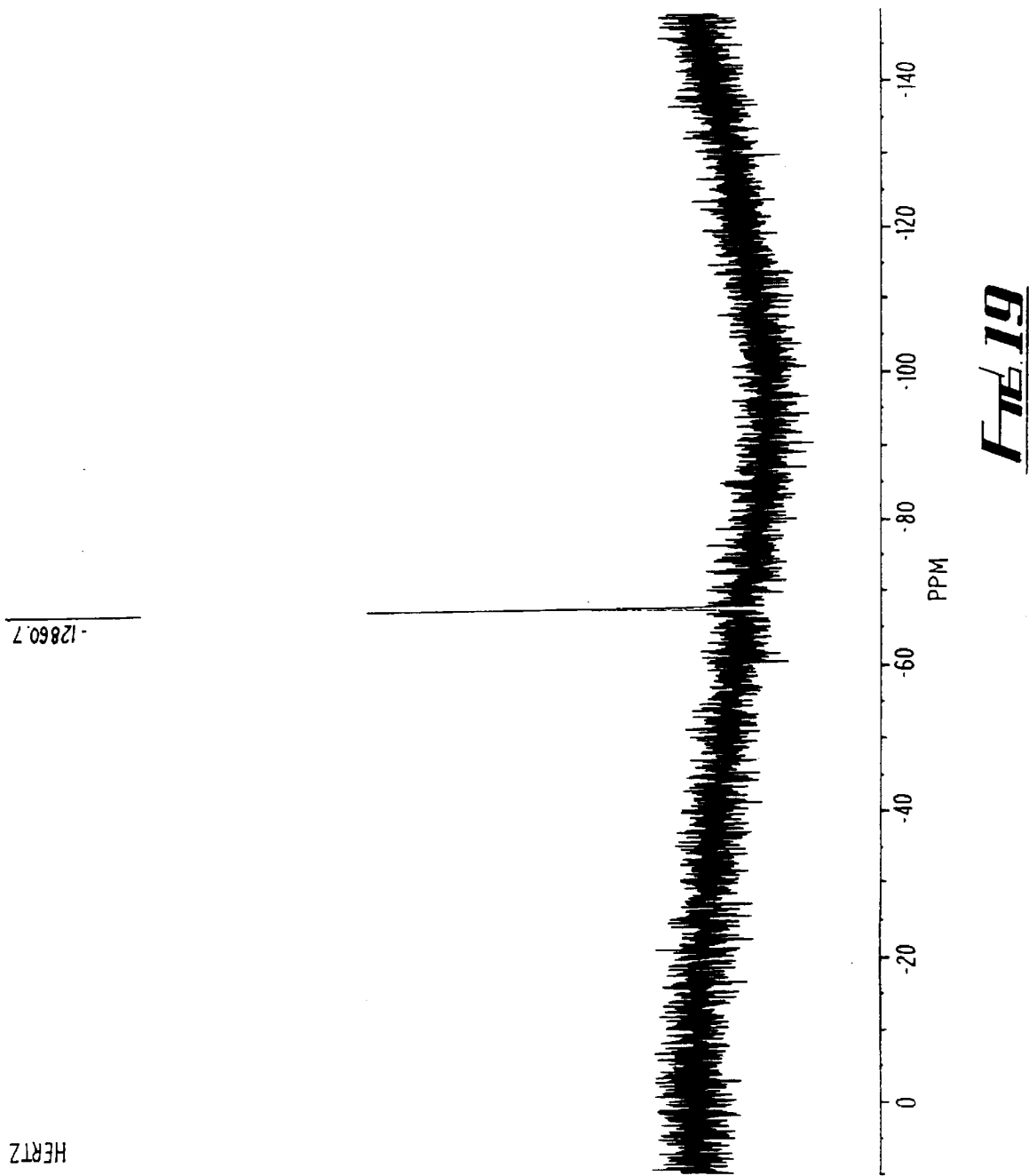
FIG. 19 illustrates $^{19}$F NMR analysis of Butyl platinic halide product.

The $^1H$ NMR of the product obtained from the reaction of the n-butyl Grinard reagent with an etheral solution of platinum (II) chloride is presented in FIG. 18. The NMR shows peaks at 0.82 ppm (doublet), 1.28 ppm (singlet), 1.39 ppm (singlet) and 1.5 ppm (singlet), relative to TMS. The spectrum is consistent with that expected for an n-butyl moiety. The $^{19}F$ NMR analysis of the material showed a singlet peak at −67 ppm (FIG. 19).

The product material was applied to a clean quartz substrate and subjected to electron beam bombardment as described in Example 2. The material was readily reduced under the influence of the electron beam to deposit a line of metallic appearance.

c) NMR Analysis of the Propyl Platinic Fluoride Material

Figure 20:
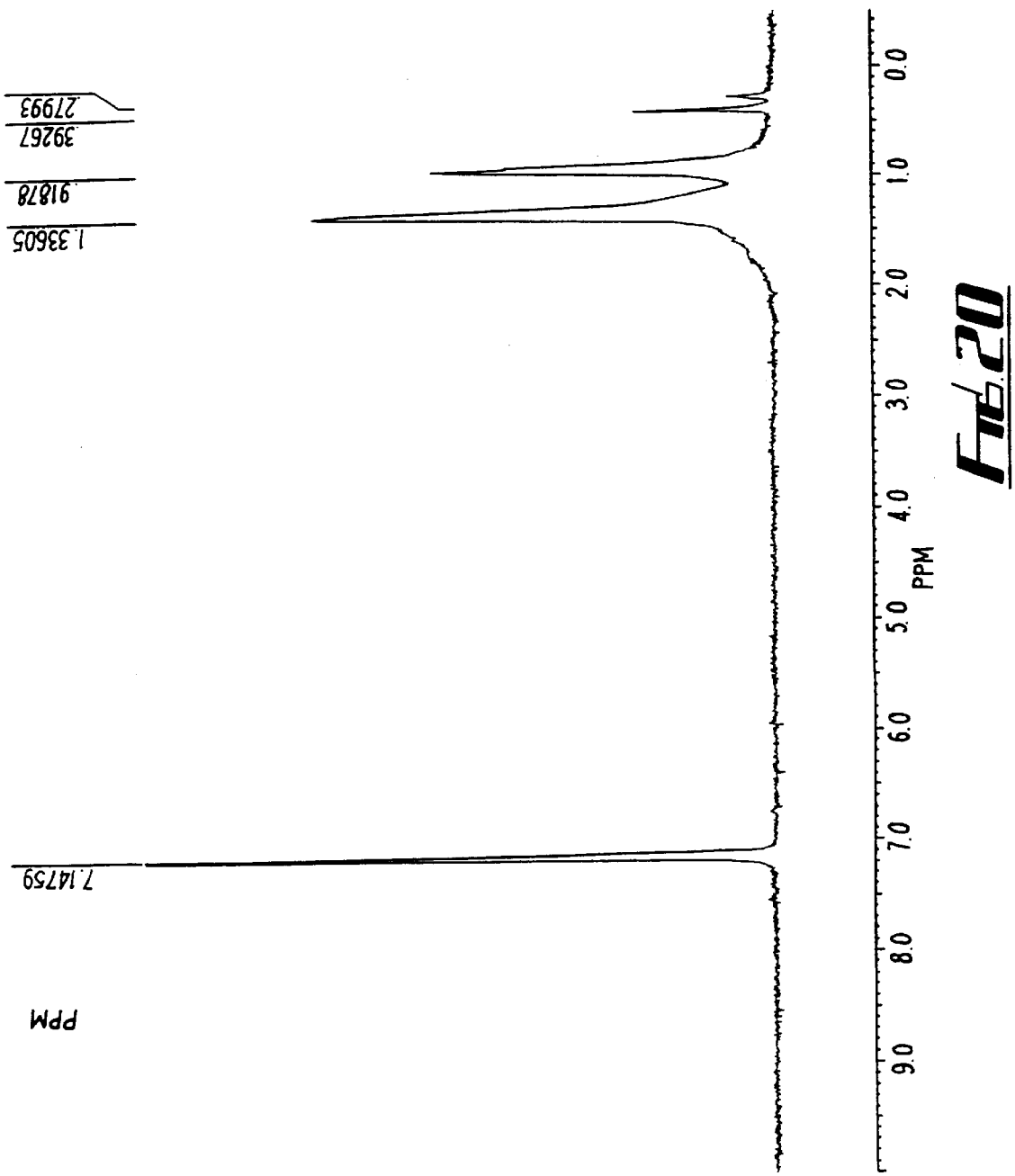
FIG. 20 illustrates $^1$H NMR analysis of Propyl platinic fluoride material.

The $^1H$ NMR spectrum was performed in deuterobenzene solvent and is presented in FIG. 20. The spectrum shows peaks at 1.33 ppm (singlet), 0.91 ppm (singlet) and 0.39 ppm (singlet) relative to TMS. The spectrum is consistent with that expected for a propyl moiety. $^{19}F$ NMR analysis gave a single peak at −67 ppm.

d) NMR Analysis of the Methylcyclohexyl Platinic Fluoride Material

Figure 21:
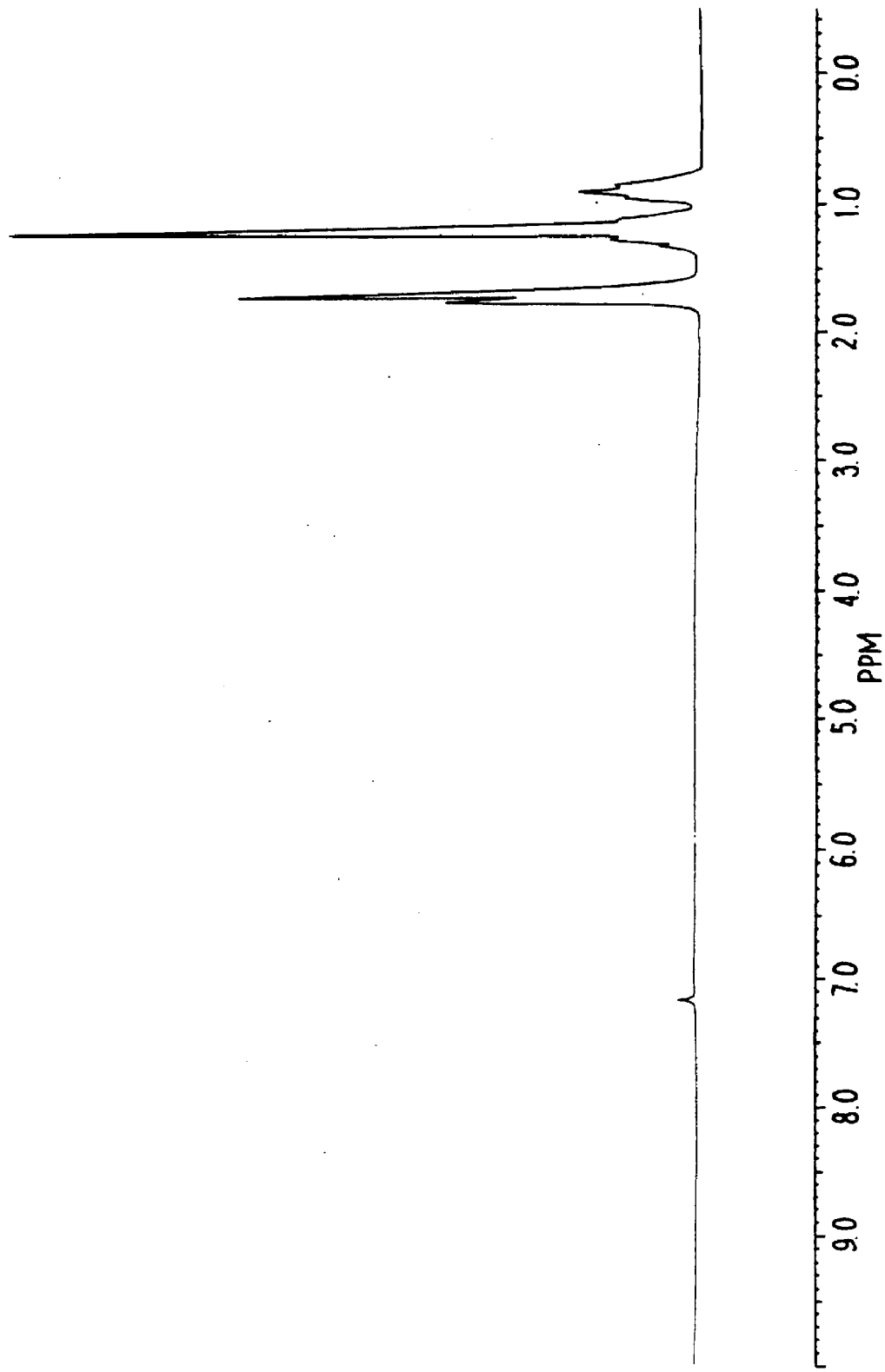
FIG. 21 illustrates $^1$H NMR analysis of Methyl cyclohexyl platinic fluoride material.
Figure 22:
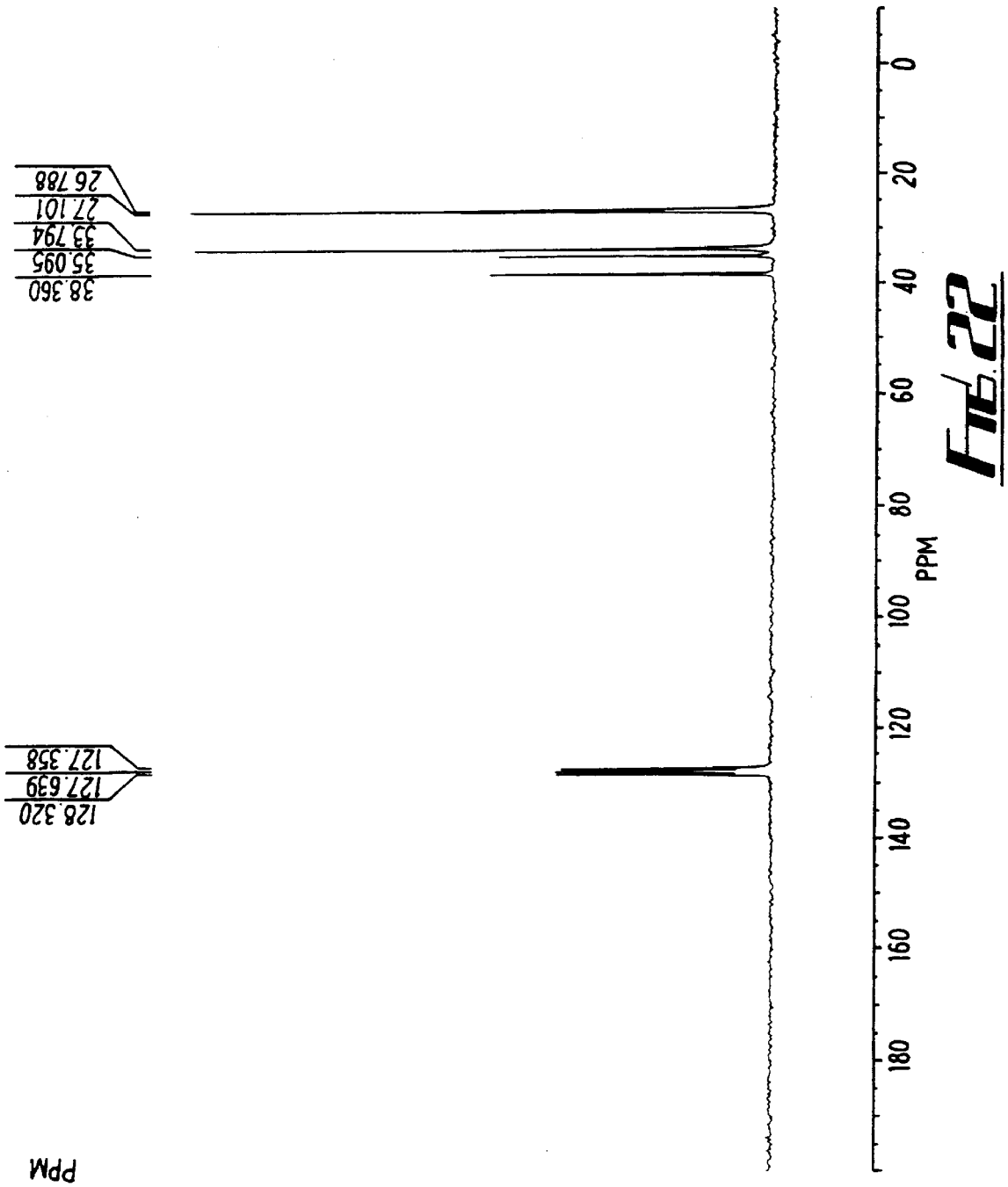
FIG. 22 illustrates $^{13}$C NMR of Methylcyclohexyl platinic fluoride material.

The $^1H$ NMR spectrum of the product material from the reaction of the methylcyclohexyl Grinard reagent with an etheral solution of platinum (II) chloride is presented in FIG. 21. The spectrum is consistent with that expected for the methylcyclohexyl ligand. The $^{13}C$ carbon NMR is also presented in FIG. 22. The spectrum also confirms that the product material contains ligated methylcyclohexyl groups.

EXAMPLE 9

Example of the Butylpalladium Analogue Complex

The preparation of the butyl palladium analogue was performed as described in Example 2. The respective organomagnesium halide intermediate material was reacted with an etheral solution of palladium (II) chloride. It was observed that the product material was thermally unstable resulting in deposition of the palladium component at around 50° C. The deposited palladium metal had strongly adhered to the glass surface and could only be removed using acids.

Results

Figure 23:
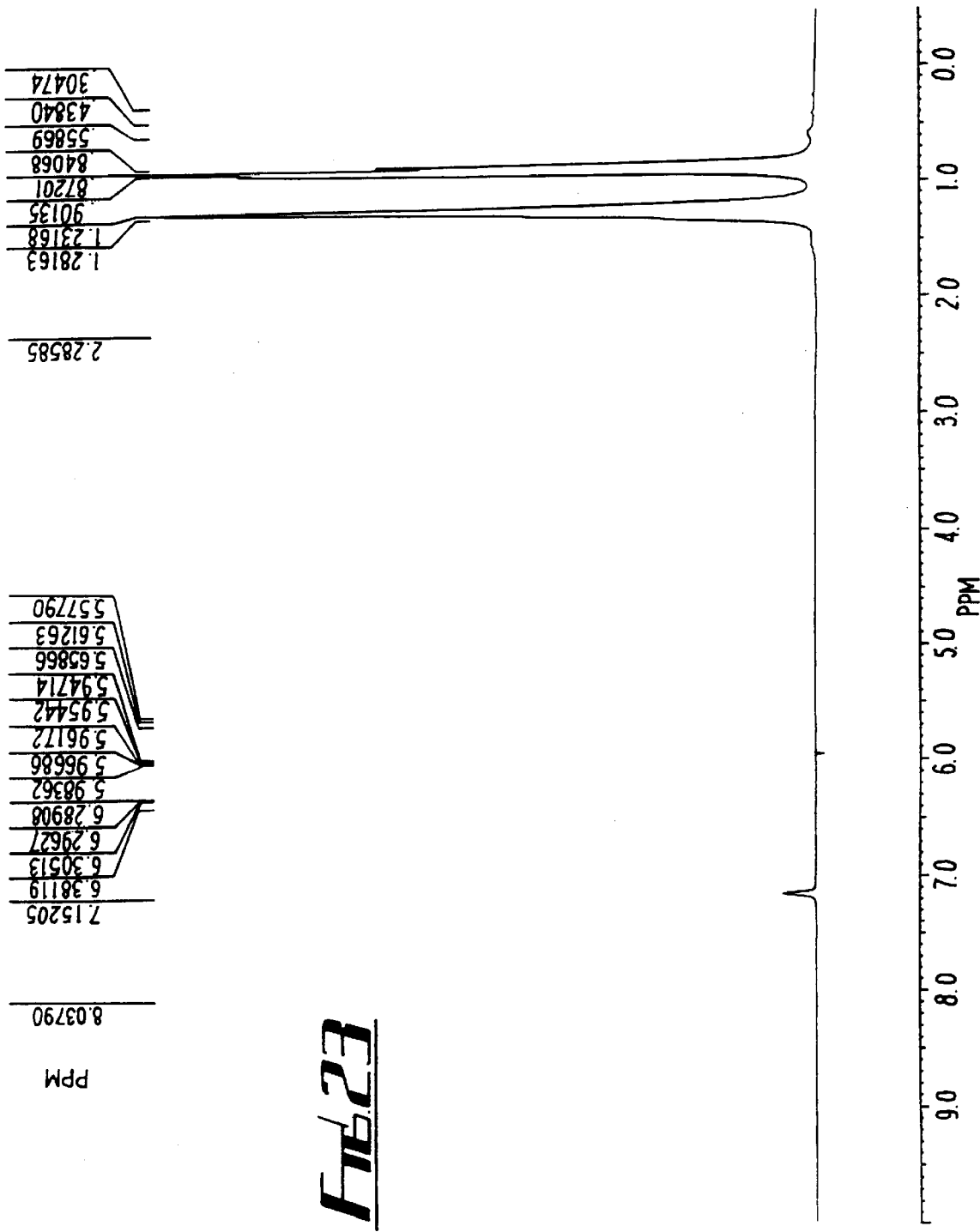
FIG. 23 illustrates $^1$H NMR analysis of Butylpalladium anologue complex.
Figure 24:
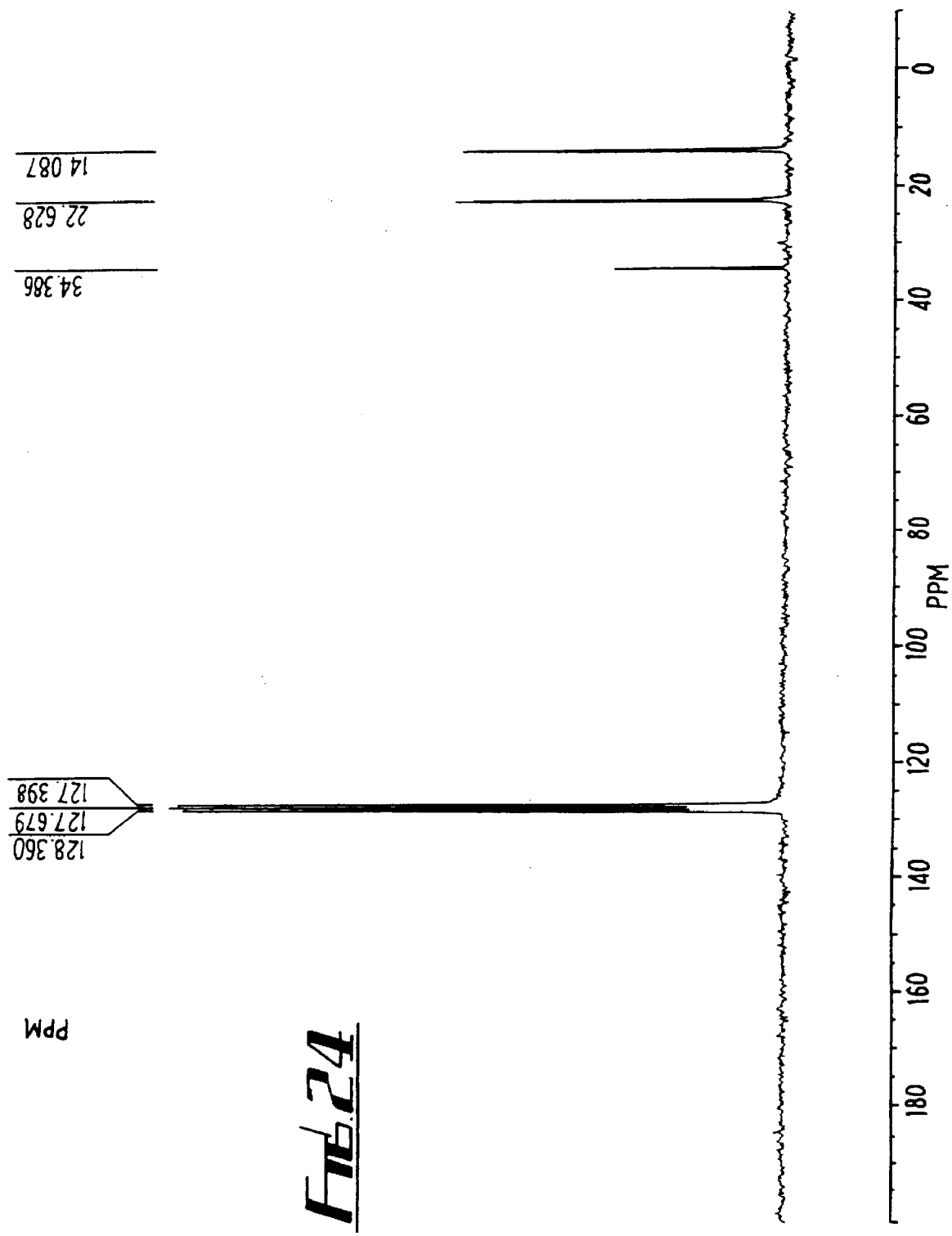
FIG. 24 shows $^{13}$C NMR spectra of Butylpalladium anologue complex.
Figure 25:
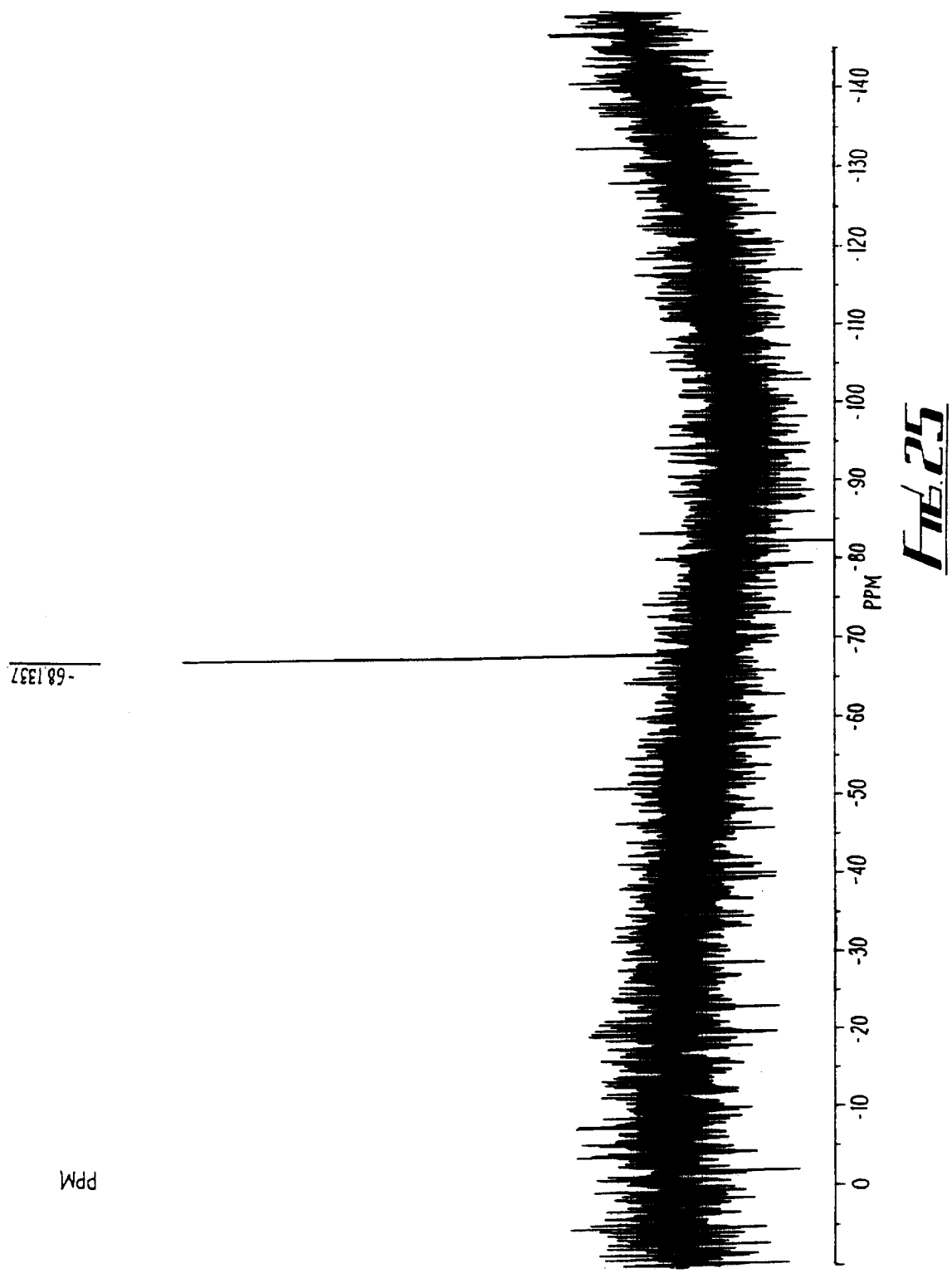
FIG. 25 illustrates $^{19}$F NMR analysis of Butylpalladium anologue complex.

The $^1$H NMR analysis of the product material from the butyl Grinard reagent with an etheral solution of palladium (II) chloride is presented in FIG. 23. The spectrum is consistent with that expected for a butyl ligand a weak interaction with the ligated centre. The $^{13}$C NMR spectra shows the presence of 3 carbon environments in the compound. The $^{19}$F NMR again shows a singlet peak at −67 ppm (FIG. 25).

General Discussion

Examples 2 to 9 show that the butyl-, propyl- and cyclohexyl- gold complexes are able to be reduced to the metal component under electron beam bombardment. The preparation of the propyl- and cyclohexyl-analogues of the gold complex show no rearrangement during the synthesis treatment. The $^1$H NMR spectra of these compounds do not exhibit any splitting patterns that are consistent with the incorporation of fluorine into the organic ligand. Whether these compounds have fluorine as a constituent in their structure remains tc be determined. The $^{19}$F NMR signal for the product materials indicate that fluorine is present in a form which confers a symetrical field around the fluorine environment. Given that fluorine has the ability to affect neighbouring carbon atoms and cause coupling over long ranges, it seems that whatever form the fluorine is in, it is shielded from the organic ligands so that coupling cannot take place.

The reaction of the n-butyl group to give sec-butyl products gives rise to some questions about the chemistry that is affecting the formation of the butylauric (III) fluoride. Firstly, it is important to note that the organic ligand itself does not contain fluorine. No splitting of the proton signals are observed in the proton spectra and there are no signals in the $^{19}$F NMR to indicate that hydrofluoroalkane groups are present. Hence, the isomerisation step of the n-alkane cannot be taking place during the fluorination process. Isomerisation usually requires the production of a carbocation species in the presence of F ions during the reaction with the methanol solution of NaF would immediately give rise to a fluorinated organic ligand, for which there is no evidence. Hence, the evidence suggests an intramolecular re-arrangement at some stage in the production of the fluorided material.

The mass spectroscopic data gives a molecular ion of 661 amu, the fragmentation pattern of which is wholly consistent with the formula $(sec\text{-}butyl)_4 Au_2 F_2$. It must be remembered that the Au (III) is in a $5d^8$ configuration that would give a square planar arrangement, and would also consider the propensity of gold to form bridging dimers. Thus, it is tentatively submitted that the tetrakis sec-butyl aurum (III) difluoride structure would be as follows:

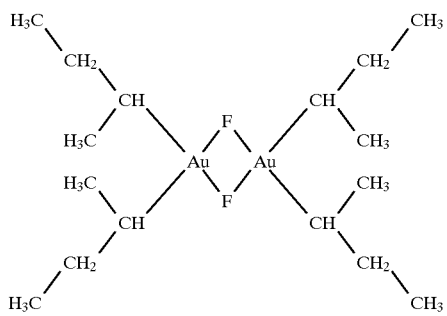

The organoaurum product is uv transparent in the region from 900–3500 nm. This is a positive result should mask-making be an application for the material.

No deposition of metal lines was obtained from the benzyl- and tertiary butyl- analogues. These materials possess good inductive properties and are able to pump electron density into neighbouring moieties. This may have an effect on the reducibility of the gold complexes.

Electron reduction has been successfully shown on the butyl analogue of the Pt material. Also the cyclohexyl analogue of the Pd materials were able to be reduced by electron beam bombardment techniques. Thermal degradation of the palladium complex at 50° C. resulted in a strongly bound metallic film of palladium that could only be removed by reaction with acid. This result indicates that the palladium analogue of the organometallic complexes is a suitable candidate for metal deposition by laser degradation.

We claim:

1. A method of chemical deposition comprising depositing on a substrate an organometallic fluoride compound which degrades under the effect of a radiant or particle beam to produce a deposit and a degraded compound residue, applying to selected areas of said compound such a radiant or particle beam and removing the degraded compound residue and unaffected compound from said substrate.

2. A method as claimed in claim 1 for manufacturing an integrated circuit wherein said deposit is a conductive material.

3. A method as claimed in claim 1 for manufacturing a photomask wherein said substrate is a transparent or translucent material and wherein said deposit is opaque.

4. A method as claimed in claim 1 wherein said compound is an organometallic gold, platinum, palladium or tin fluoride.

5. A method as claimed in claim 1 wherein said compound is tetra-sec butyl diaurum difluoride.

6. A method as claimed in claim 1 wherein said compound is exposed to microwave radiation after application to said substrate and before application of said radiant or particle beam.

7. A method as claimed in claim 1 wherein said compound is applied to said substrate by an organometallic vapour deposition (OMVD) technique.

8. A method as claimed in claim 1 wherein said compound is degraded by a laser beam, an ultra-violet beam and/or an electron beam.

9. Use of a radiant or particle beam in the method as claimed in claim 1.

* * * * *